(12) United States Patent
Franklin

(10) Patent No.: US 9,107,870 B2
(45) Date of Patent: Aug. 18, 2015

(54) ANGIOTENSIN PEPTIDES IN TREATING MARFAN SYNDROME AND RELATED DISORDERS

(71) Applicant: TARIX PHARMACEUTICALS LTD, Cambridge, MA (US)

(72) Inventor: Richard Franklin, Cambridge, MA (US)

(73) Assignee: Tarix Phamaceuticals Ltd., Cambridge, MA (US)

( * ) Notice: Subject to any disclaimer, the term of this patent is extended or adjusted under 35 U.S.C. 154(b) by 0 days.

(21) Appl. No.: 14/506,489

(22) Filed: Oct. 3, 2014

(65) Prior Publication Data

US 2015/0031634 A1    Jan. 29, 2015

Related U.S. Application Data

(60) Provisional application No. 61/827,271, filed on May 24, 2013.

(51) Int. Cl.
*A61K 38/08* (2006.01)
*A61K 31/4178* (2006.01)
*A61K 45/06* (2006.01)

(52) U.S. Cl.
CPC ........... *A61K 38/085* (2013.01); *A61K 31/4178* (2013.01); *A61K 45/06* (2013.01)

(58) Field of Classification Search
CPC .................................................. A61K 38/085
See application file for complete search history.

(56) References Cited

U.S. PATENT DOCUMENTS

| | | | |
|---|---|---|---|
| 4,244,946 A | 1/1981 | Rivier et al. | |
| 4,305,872 A | 12/1981 | Johnston et al. | |
| 4,316,891 A | 2/1982 | Guillemin et al. | |
| 5,182,264 A * | 1/1993 | Watkins | 514/15.6 |
| 6,235,766 B1 | 5/2001 | Heitsch et al. | |
| 2010/0055146 A1 | 3/2010 | Haas et al. | |
| 2011/0281805 A1 | 11/2011 | Walther et al. | |
| 2012/0172301 A1 | 7/2012 | Ocaranza Jeraldino et al. | |

FOREIGN PATENT DOCUMENTS

| | | |
|---|---|---|
| EP | 2264048 A2 | 12/2010 |
| WO | WO-98/02452 A2 | 1/1998 |
| WO | WO-01/53331 A2 | 7/2001 |
| WO | WO 2007050793 A2 * | 5/2007 |
| WO | WO-2013/032784 A1 | 3/2013 |

OTHER PUBLICATIONS

Daugherty et al., "Angiotensin II promotes atherosclerotic lesions and aneurysms in apolipoprotein E-deficient mice", J. Clin. Invest., 2000, pp. 1605-1612.*
Tom et al.,"Bradykinin Potentiation by Angiotensin-(1-7) and ACE Inhibitors Correlates With ACE C- and N-Domain Blockade", Hypertension, 2001, pp. 95-99.*
Serreau et al., "Developmental toxicity of the angiotensin II type 1 receptor antagonists during human pregnancy: a report of 10 cases", BJOG: an International Journal of Obstetrics and Gynaecology, Jun. 2005, pp. 710-712.*
Cook et al.,"Angiotensin-(1-7) Reduces Fibrosis in Orthotopic Breast Tumors", Cancer Res; 70(21); pp. 8319-8328; 2010.*
Bruemmer et al., "Relevance of angiotensin II-induced aortic pathologies in mice to human aortic aneurysms", Ann. N.Y. Acad. Sci., 2011, pp. 7-10.*
Altschul, S. and Gish, W., Local alignment statistics, Methods in Enzymology, 266:460-480 (1996).
Bodanszky, M. and Sheehan, J. et al., Active esters and resins in peptide synthesis, Chemistry and Industry (London), 38:1597 (1966).
Brady, L. and Dodson, G., Drug design. Reflections on a peptide, Nature 368(6473):692-693 (1994).
Evans, B. et al., Design of nonpeptidal ligands for a peptide receptor: cholecystokinin antagonists, Journal of Medicinal Chemistry, 30(7):1229-1239 (1987).
Fauchere, J. et al., Association with HeLa cells of *Campylobacter jejuni* and *Campylobacter coli* isolated from human feces, Infection and Immunity, 54(2):283-287 (1986).
Galande, A. et al., Understanding base-assisted desulfurization using a variety of disulfide-bridged peptides, Biopolymers, 71(5):534-551 (2003).
Godeny, M. and Sayeski, P., ANG II-induced cell proliferation is dually mediated by c-Src/Yes/Fyn-regulated ERK1/2 activation in the cytoplasm and PKCzeta-controlled ERK1/2 activity within the nucleus, American Journal of Physiology—Cell Physiology, 291(6):C1297-1307 (2006).
Hudson, D. et al., Methionine enkephalin and isosteric analogues. I. Synthesis on a phenolic resin support, International Journal of Peptide Protein Research, 14:177-185 (1979).
International Search Report for PCT/US2014/39141, 4 pages (Oct. 24, 2014).
Jameson, B. et al., A rationally designed CD4 analogue inhibits experimental allergic encephalomyelitis, Nature 368(6473):744-746 (1994).
Koziarz, P. et al., Reciprocal modulation of the binding of angiotensin agonists and antagonists to angiotensin receptors in smooth muscle, General Pharmacology, 24(3):705-713 (1933).
Lacro, R.V. et al., Atenolol versus Losartan in Children and Young Adults with Marfan's Syndrome, The New England Journal of Medicine, 371(22):2061-2071 (2014).
Lautner, R. et al., Discovery and characterization of alamandine: a novel component of the renin-angiotensin system, Circulation Research, 112(8):1104-1111 (2013).

(Continued)

Primary Examiner — Karlheinz R Skowronek
Assistant Examiner — Lianko Garyu
(74) Attorney, Agent, or Firm — Choate, Hall & Stewart LLP; Fangli Chen; Brian E. Reese

(57) ABSTRACT

The present invention provides, among other things, methods of treating Marfan Syndrome and/or a Marfan-related disorder including administering to a subject suffering from or susceptible to Marfan Syndrome and/or a Marfan-related disorder an angiotensin (1-7) peptide. In some embodiments, the angiotensin (1-7) peptide is administered at an effective dose periodically at an administration interval such that at least one symptom or feature of Marfan Syndrome and/or a Marfan-related disorder is reduced in intensity, severity, duration, or frequency or has delayed in onset.

14 Claims, 1 Drawing Sheet

(56) References Cited

OTHER PUBLICATIONS

Merrifield, R.B., Solid Phase Peptide Synthesis, Journal of the American Chemical Society, 85:2149-2154 (1963).

Powell, M. et al., Peptide stability in drug development. II. Effect of single amino acid substitution and glycosylation on peptide reactivity in human serum, Pharmaceutical Research, 10(9):1268-1273 (1993).

Rizo, J. and Gierasch, L., Constrained peptides: models of bioactive peptides and protein substructures, Annual Review of Biochemistry, 61:387-418 (1992).

Sarr, M. et al., Red wine polyphenols prevent angiotensin II-induced hypertension and endothelial dysfunction in rats: role of NADPH oxidase, Cardiovascular Research, 71(4):794-802 (2006).

Spatola, A. et al., Structure-activity relationships of enkephalins containing serially replaced thiomethylene amide bond surrogates, Life Sciences, 38(14):1243-1249 (1986).

Vale, W. et al., Characterization of a 41-residue ovine hypothalamic peptide that stimulates secretion of corticotropin and beta-endorphin, Science, 213(4514):1394-1397 (1981).

Written Opinion for PCT/US2014/39141, 9 pages (Oct. 24, 2014).

Xiong, W. et al., Doxycycline delays aneurysm rupture in a mouse model of Marfan syndrome, Journal of Vascular Surgery, 47(1):166-172 (2008).

Yuan, S. and Jing, H. et al., Cardiac pathologies in relation to Smad-dependent pathways, Interactive CardioVascular and Thoracic Surgery, 11(4): 455-460 (2010).

Zeng, W. et al., Impairment of Cardiac Function and Remodeling Induced by Myocardial Infarction in Rats are Attenuated by the Nonpeptide Angiotensin-(1-7) Analog AVE 0991, Cardiovascular Therapeutics, 30(3): 152-161 (2012).

* cited by examiner

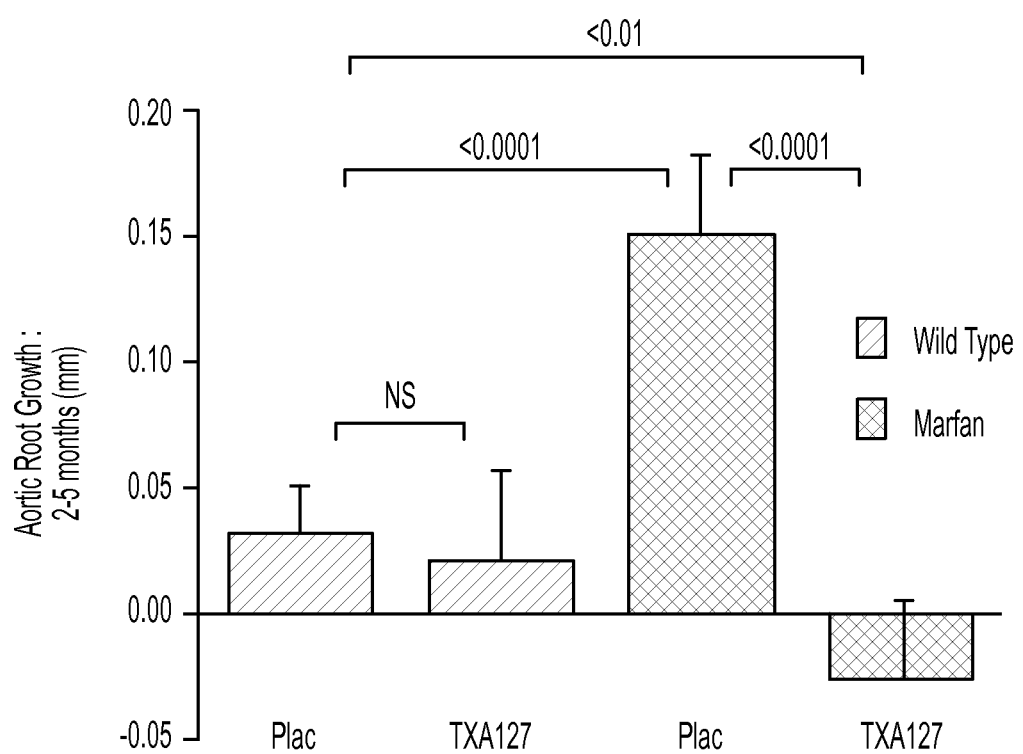

ANGIOTENSIN PEPTIDES IN TREATING MARFAN SYNDROME AND RELATED DISORDERS

CROSS-REFERENCE TO RELATED APPLICATIONS

This application is a continuation of International Application No. PCT/US14/39141, filed May 22, 2014, which claims priority to U.S. provisional patent application 61/827,271, filed May 24, 2013, the disclosures of which are hereby incorporated by reference in their entirety.

The instant application contains a Sequence Listing which has been submitted electronically in ASCII format and is hereby incorporated by reference in its entirety. Said ASCII copy, created on Jan. 28, 2015, is named 2011433-0019_SL.txt and is 11,346 bytes in size.

BACKGROUND

Marfan syndrome is a connective tissue disorder that affects approximately 1 in 5,000 individuals and is an inherited autosomal dominant disease that is caused by mutations in the gene encoding fibrillin-1 (FBN1), an extracellular matrix protein. Marfan Syndrome can manifest in a variety of ways, often affecting one or more of ocular tissue, cardiovascular tissue, and skeletal tissue. Most serious are cardiac effects, which may lead to aortic dilation and dissection, resulting in death without rapid and invasive treatment.

Prior to the present invention, there were no known effective therapies for Marfan Syndrome. Instead, treatment of Marfan sufferers was limited to supportive treatment of symptoms as they develop.

SUMMARY OF THE INVENTION

The present invention provides, among other things, methods and compositions for treating connective tissue diseases, disorders, or conditions including Marfan Syndrome and Marfan-related disorders. The present invention is based, at least in part, on the realization that angiotensin (1-7) peptides and/or angiotensin (1-7) receptor agonists may be used to treat one or more symptoms of Marfan Syndrome and related connective tissue disorders. While angiotensin (1-7) peptides were known to be effective for promoting angiogenesis (vascular tissue), prior to the present invention it was unknown that angiotensin (1-7) peptides could improve one or more symptoms of connective tissue disorders such as Marfan Syndrome.

In some embodiments, the present invention provides methods of treating Marfan Syndrome and/or a Marfan-related disorder including administering to a subject suffering from or susceptible to Marfan Syndrome and/or a Marfan-related disorder an angiotensin (1-7) peptide. In some embodiments, the angiotensin (1-7) peptide is administered at an effective dose periodically at an administration interval such that at least one symptom or feature of Marfan Syndrome and/or a Marfan-related disorder is reduced in intensity, severity, duration, or frequency or has delayed in onset. In some embodiments, the at least one symptom or feature of Marfan Syndrome and/or a Marfan-related disorder is selected from the group consisting of aortic enlargement, aortic dissection, eye lens dislocation, mitral valve prolapse, joint hypermobility, retinal detachment, strabismus, cataracts, glaucoma, obstructive lung disease, scoliosis, temporomandibular joint disorder, dural ectasia, and osteopenia.

In addition to the treatment of Marfan Syndrome itself, the present invention also provides methods of treating a variety of Marfan-related disorders. In some embodiments, the Marfan-related disorder is selected from the group consisting of: Loeys-Dietz Syndrome, Familial Aortic Aneurysm, Bicuspid Aortic Valve with Aortic Dilation, Familial Ectopia Lentis (dislocated lens), Mitral Valve Prolapse Syndrome, Marfan Habitus, Congenital Contractural Arachnodactyly (Beals Syndrome), Stickler syndrome, Shprintzen-Goldberg syndrome, Weill-Marchesani syndrome, and Ehlers-Danlos syndrome.

According to various embodiments, angiotensin (1-7) peptides may be administered via any of a variety of routes. In some embodiments, the angiotensin (1-7) peptide is administered parenterally. In some embodiments, the parenteral administration is selected from intravenous, intradermal, inhalation, transdermal (topical), intraocular, intramuscular, subcutaneous, intramuscular, and/or transmucosal administration. In some embodiments, the angiotensin (1-7) peptide is administered orally. In some embodiments, an angiotensin (1-7) peptide is administered according to an administration interval. In some embodiments, the angiotensin (1-7) peptide is administered monthly, weekly, daily, or at variable intervals.

It is contemplated that various embodiments may use different amounts of angiotensin (1-7) peptide. In some embodiments, the angiotensin (1-7) peptide is administered at an effective dose ranging from about 1-1,000 µg/kg/day. In some embodiments, the angiotensin (1-7) peptide is administered at an effective dose ranging from about 50-500 µg/kg/day. In some embodiments, the angiotensin (1-7) peptide is administered at an effective dose ranging from about 400-500 µg/kg/day. In some embodiments, the angiotensin (1-7) peptide is administered at an effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 µg/kg/day.

In some embodiments, an angiotensin (1-7) peptide may be used with one or more medications used to treat Marfan Syndrome or Marfan-related disorders or one or more symptoms thereof. In some embodiments, the one or more Marfan Syndrome and/or a Marfan-related disorder medications is selected from the group consisting of beta blockers, calcium channel blockers, ACE inhibitors, angiotensin II receptor antagonists (e.g. losartan), anticoagulants, and combinations thereof.

It is contemplated that various angiotensin (1-7) peptides may be used in various embodiments. In some embodiments, the angiotensin (1-7) peptide comprises the naturally-occurring Angiotensin (1-7) amino acid sequence of $Asp^1$-$Arg^2$-$Val^3$-$Tyr^4$-$Ile^5$-$His^6$-$Pro^7$ (SEQ ID NO:1).

In some embodiments, the angiotensin (1-7) peptide is a functional equivalent of SEQ ID NO:1. In some embodiments, the functional equivalent is a linear peptide. In some embodiments, the linear peptide comprises a sequence that includes at least four amino acids from the seven amino acids that appear in the naturally-occurring Angiotensin (1-7), wherein the at least four amino acids maintain their relative positions as they appear in the naturally-occurring Angiotensin (1-7). In some embodiments, the linear peptide contains 4-25 amino acids. In some embodiments, the linear peptide is a fragment of the naturally-occurring Angiotensin (1-7). In some embodiments, the linear peptide contains amino acid substitutions, deletions and/or insertions in the naturally-occurring Angiotensin (1-7). In some embodiments, the linear peptide has an amino acid sequence of $Asp^1$-$Arg^2$-$Val^3$-$Ser^4$-$Ile^5$-$His^6$-$Cys^7$ (SEQ ID NO:2).

In some embodiments, the functional equivalent is a cyclic peptide. In some embodiments, the cyclic peptide comprises a linkage between amino acids. In some embodiments, the linkage is located at residues corresponding to positions $Tyr^4$ and $Pro^7$ in naturally-occurring Angiotensin (1-7). In some embodiments, the linkage is a thioether bridge. In some embodiments, the cyclic peptide comprises an amino acid sequence otherwise identical to the naturally-occurring Angiotensin (1-7) amino acid sequence of $Asp^1$-$Arg^2$-$Val^3$-$Tyr^4$-$Ile^5$-$His^6$-$Pro^7$ (SEQ ID NO:1). In some embodiments, the cyclic peptide is a 4,7-cyclized angiotensin (1-7) with the following formula:

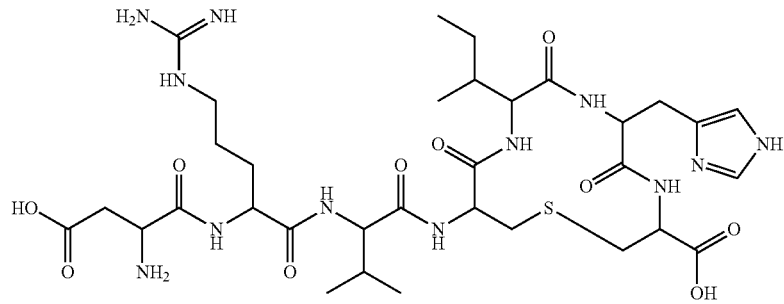 [SMILES: CCC(C)C1NC(=O)C(NC(=O)C(NC(=O)C(CCCNC(=N)N)NC(=O)C(N)CC(=O)O)C(C)C)CSCC(C(=O)O)NC(=O)C(Cc2c[nH]cn2)NC1=O]

In some embodiments, the angiotensin (1-7) peptide comprises one or more chemical modifications to increase protease resistance, serum stability and/or bioavailability. In some embodiments, the one or more chemical modifications comprise pegylation.

In some embodiments, the present invention provides methods of treating Marfan Syndrome and/or a Marfan-related disorder including administering to a subject who is suffering from or susceptible to Marfan Syndrome and/or a Marfan-related disorder an angiotensin (1-7) receptor agonist. In some embodiments, the angiotensin (1-7) receptor agonist is a non-peptidic agonist. In some embodiments, the non-peptidic agonist is a compound with the following structure:

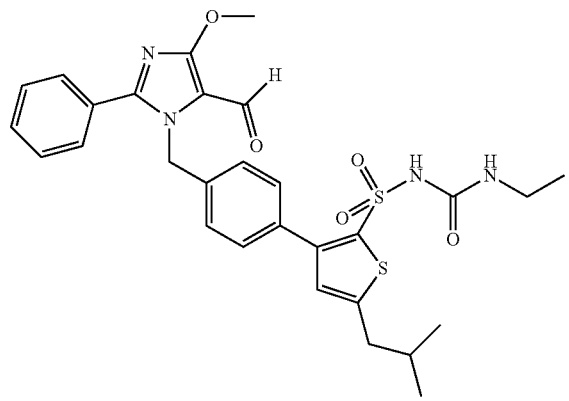 [SMILES: CCNC(=O)NS(=O)(=O)c1sc(CC(C)C)cc1-c1ccc(Cn2c(-c3ccccc3)nc(OC)c2C=O)cc1]

or a pharmaceutically acceptable salt thereof. In some embodiments, the angiotensin (1-7) receptor agonist is administered orally.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

FIG. 1 shows an exemplary graph of aortic root growth as determined from echocardiogram data generated from wild-type or $Fbn1^{C1039G+}$ mice exposed to 500 μg/kg/day TXA127 or placebo for 60 days.

DEFINITIONS

In order for the present invention to be more readily understood, certain terms are first defined below. Additional definitions for the following terms and other terms are set forth throughout the specification.

Agonist: As used herein, the term "agonist" refers to any molecule that has a positive impact in a function of a protein of interest. In some embodiments, an agonist directly or indirectly enhances, strengthens, activates and/or increases an activity of a protein of interest. In particular embodiments, an agonist directly interacts with the protein of interest. Such agonists can be, e.g., proteins, chemical compounds, small molecules, nucleic acids, antibodies, drugs, ligands, or other agents.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion. In certain embodiments, a peptide has no intrinsic biological activity but that inhibits the effects of one or more naturally-occurring angiotensin compounds is considered to be biologically active.

Carrier or diluent: As used herein, the terms "carrier" and "diluent" refers to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, the therapeutic agent is administered continuously over a predetermined period. In some embodiments, the therapeutic agent is administered once a day (QD) or twice a day (BID).

Functional equivalent or derivative: As used herein, the term "functional equivalent" or "functional derivative" denotes a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of disease as the individual being treated, who is about the same age as the individual being treated (to ensure that the stages of the disease in the treated individual and the control individual(s) are comparable).

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Prevent: As used herein, the term "prevent" or "prevention", when used in connection with the occurrence of a disease, disorder, and/or condition, refers to reducing the risk of developing the disease, disorder and/or condition. See the definition of "risk."

Polypeptide: The term "polypeptide" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., Marfan Syndrome or a Marfan-related disorder). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., Marfan Syndrome or a Marfan-related disorder). In some embodiments a reference sample or group of reference samples are from individuals comparable to a particular individual. In some embodiments, relative risk is 0, 1, 2, 3, 4, 5, 6, 7, 8, 9, 10, or more.

Stability: As used herein, the term "stable" refers to the ability of the therapeutic agent to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In certain embodiments, pharmaceutical compositions described herein have been formulated such that they are capable of stabilizing, or alternatively slowing or preventing the degradation, of one or more therapeutic agents formulated therewith. In the context of a formulation a stable formulation is one in which the therapeutic agent therein essentially retains its physical and/or chemical integrity and biological activity upon storage and during processes (such as freeze/thaw, mechanical mixing and lyophilization).

Subject: As used herein, the term "subject" refers to a human or any non-human animal (e.g., mouse, rat, rabbit, dog, cat, cattle, swine, sheep, horse or primate). A human includes pre and post natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, Muscular Dystrophy) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION OF CERTAIN EMBODIMENTS

The present invention provides, among other things, improved compositions and methods for treating or reducing the risk of connective tissue diseases, disorders and/or conditions such as Marfan Syndrome and Marfan-related disorders.

Various aspects of the invention are described in detail in the following sections. The use of sections is not meant to limit the invention. Each section can apply to any aspect of the invention. In this application, the use of "or" means "and/or" unless stated otherwise.

Marfan Syndrome

Marfan Syndrome is a systemic connective tissue disorder resulting from one or more mutations in the fibrillin-1 (FBN-1) gene. Such mutations result in a variable constellation of symptoms with at least one thing in common, expansion of one or more tissues beyond normal limits. For example, one of the most serious symptoms of Marfan Syndrome is aortic dilation and is caused by stretching of the cardiac tissue to the point that mechanical stability and or mechanical compliance is compromised, potentially leading to failure such as aortic dissection.

Marfan Syndrome is largely an inherited condition and is autosomal dominant, though it is suspected that approximately 25% of Marfan sufferers manifest the disease as a result of spontaneous mutation. It is suspected that dysregulation of FBN1 results in increased TGF-β signaling.

Many Marfan sufferers exhibit a constellation of skeletal symptoms known as Marfanoid Habitus (Marfan body type, described below). In addition to Marfanoid Habitus or similar symptomatic presentation, Marfan sufferers may exhibit a wide array of other symptoms including, but not limited to aortic enlargement, aortic dissection, eye lens dislocation, mitral valve prolapse, retinal detachment, strabismus, cataracts, glaucoma, obstructive lung disease, scoliosis, temporomandibular joint disorder, dural ectasia, and osteopenia.

Current treatments for Marfan sufferers are generally limited to supportive treatments, including treatment of symptoms as they arise. As an example of symptomatic treatments, development of cardiac abnormalities caused by Marfan Syndrome are typically treated with beta blockers to cause the heart to beat slower and with less force in order to slow the progression of aortic dilation. Once aortic dilation has progressed, surgery is often used to replace the dilated segment before it tears as tearing can lead to death in minutes. Without wishing to be held to a particular theory, it is thought that vascular pathology in Marfan Syndrome is associated with changes in connective tissue architecture manifested by reduced mechanical compliance, abnormal extracellular matrix modeling, and progressive aneurysm development that ultimately lead to aortic wall degradation.

Marfanoid Habitus

Marfanoid Habitus is a Marfan-related disorder that typically includes the symptoms of long limbs, arachnodactyly, and hyperlaxity of joints (i.e. joint hypermobility). Other symptoms common among Marfanoid Habitus sufferers include scoliosis, chest wall abnormalities, flat feet, and a highly arched roof of the mouth, though others may be exhibited as well. Sufferers of Marfanoid Habitus tend not to manifest the aortic and ocular issues common among Marfan sufferers. In general, the skeletal issues comprising Marfanoid Habitus are not life-threatening, but do cause significant discomfort and even disability in affected individuals.

Loeys-Dietz Syndrome

Loeys-Dietz Syndrome is an autosomal dominant genetic disorder which shares may features with Marfan Syndrome, including scoliosis, joint hypermobility, and congenital heart problems. However, the genetic basis of Loeys-Dietz Syndrome is one or more mutations in the genes encoding transforming growth factor beta receptor-1 or -2 (TGFBR1 or TGFBR2, respectively), rather than a mutation in the FBN1 gene as in Marfan Syndrome.

Sufferers of Loeys-Dietz Syndrome may exhibit symptoms distinct from Marfan sufferers. These symptoms include but are not limited to widely spaced eyes, cleft palate, club foot and translucency of the skin. As with Marfan Syndrome, there are no known cures for the disorder, and cardiac abnormalities, including aortic aneurysm and dissection are the most serious effects of Loeys-Dietz.

Congenital Contractural Arachnodactyly (Beals Syndrome)

Beals Syndrome is a Marfan-Related disorder having as its genetic basis one or more mutations in the fibrillin-2 (FBN-2) gene, as opposed to FBN-1 mutation(s) underlying Marfan Syndrome. Beals Syndrome sufferers typically experience contractures at birth, with the degree ranging from mild contracture of large joints such as the elbow and/or knee, to large contractures resulting in scoliosis and sometimes even kyphosis. Severe contractures are typically treated via surgery.

Sufferers of Beals Syndrome typically have long, thin fingers and toes with contractures limiting or even preventing straightening of digits. Also, sufferers often have unusual ears that appear crumpled and may experience joint dislocation, often in the knee (patellar dislocation). In some cases, contractures may be present from birth and reduce in severity over time, though some sufferers do not experience significant reductions in contracture. In some cases, contractures may be so severe as to fracture long bones, though this is not typical.

Beals Syndrome may be diagnosed through observation of crumpled ears and other congenital contractures, something not typically observed in Marfan sufferers. Additionally, Beals sufferers do not usually manifest the ocular and cardiovascular complications seen in Marfan sufferers.

Stickler Syndrome

Stickler Syndrome is a Marfan-Related disorder of the connective tissue, specifically collagen. Stickler syndrome is most often characterized by distinctive facial abnormalities, ocular problems, and joint problems. Unlike Marfan Syndrome, it appears that more than one gene may be affected in Stickler sufferers. Mutations in the COL2A1, COL11A1, COL11A2, and COL9A1 genes have all been reported, with mutation(s) in COL2A1 being most common (found in ~75% of Stickler sufferers).

A characteristic feature of Stickler Syndrome is a flattened facial appearance. This is thought to be caused by underdeveloped bones in the middle of the face, including the cheekbones and bridge of the nose. It is also common for Stickler sufferers to exhibit a constellation of symptoms known as the Pierre Robin sequence. The Pierre Robin sequence includes a U-shaped or even V-shaped cleft palate, a small lower jaw, and a tongue too large for the space formed by the small lower jaw. It is somewhat common for Stickler sufferers to have an obstructed airway due to the Pierre Robin sequence.

The most common treatment employed on behalf of Stickler sufferers is surgery to correct maxillofacial defects and clear obstructed airways. In addition, pain medications are sometimes required to alleviate discomfort due to malformed anatomy.

Shprintzen-Goldberg Syndrome

Shprintzen-Goldberg Syndrome (SGS) is an extremely rare multiple anomaly syndrome that typically includes craniosynostosis, multiple abdominal hernias, cognitive impairment, and other skeletal malformations. There is uncertainty about the cause of the disorder with some reports linking development to the FBN1 gene, and others finding no such causal link.

In contrast to Marfan Syndrome, SGS sufferers do exhibit cognitive defects and brain anomalies such as hydrocephalus and dilation of the lateral ventricles. Diagnosis is at times complicated by the fact that SGS sufferers may also exhibit cardiovascular anomalies including mitral valve prolapse, aortic regurgitation, and skeletal abnormalities including arachnodactyly, scoliosis, joint hypermobility, sometimes resulting in difficulty in diagnosing over Marfan Syndrome or other Marfan-related disorders.

As with other Marfan-related disorders, treatment of SGS is limited to symptomatic treatments including surgery, physiotherapy, and pain management.

Weill-Marchesani Syndrome

Weill-Marchesani Syndrome (WMS) is a Marfan-related connective tissue disorder that is characterized by short stature, broad head and other face and hand abnormalities including short fingers and small, spherical lenses of the eye that are particularly susceptible to dislocation. The average height of male sufferers is between four feet eight inches to five feet six inches, while female suffers tend to range between four feet three inches to five feet two inches.

While WMS sufferers may have mutations in their FBN1 gene, mutations in the ADAMTS10 gene are also common, and there have been cases where WMS sufferers had no mutation in either their FBN1 or ADAMTS10 genes. Reported cases have had both autosomal dominant and autosomal recessive manifestations. As a result of this genetic variability, the cause of WMS is poorly understood. As with several Marfan-related disorders, treatment is mostly supportive in nature and there is no known cure.

Ehlers-Danlos Syndrome

Ehlers-Danlos Syndrome is a Marfan-related connective tissue disorder characterized by one or more defects in the synthesis of collagen (type I or III). The severity of the defect leads to a wide range of symptoms that can be mild or life-threatening, depending upon the specific clinical manifestation. The symptoms are similar to those found in other Marfan-related syndromes including hyper flexible joints, scoliosis, and various cardiovascular abnormalities. As with other Marfan-related disorders, there is no cure and treatments are supportive in nature.

Unlike Marfan Syndrome, Ehlers-Danlos sufferers may also exhibit assorted skin-related conditions including fragile skin that tears easily, abnormal wound healing, and fatty growths on forearms and/or shins. The range of symptoms exhibited by Ehlers-Danlos sufferers may be due to the wide range of genetic abnormalities that may play a role in development of the disorder including COL1A1, COL1A2, COL3A1, COL5A1, COL5A2, and TNXB. Mutation of these genes is known to affect one or more of the structure, processing or production of proper collagen.

Familial Aortic Aneurysm

Familial Aortic Aneurysm is a Marfan-related disorder that often manifests in Marfan sufferers. It is an autosomal dominant disorder of large arteries. Familial aortic aneurysm is caused by a breakdown of collagen, elastin and smooth muscle that can be caused by normal aging in addition to genetic abnormalities such as that underlying Marfan Syndrome. Aortic aneurysm results in a significantly increased risk of aortic dissection, which can quickly lead to death.

Bicuspid Aortic Valve with Aortic Dilation

A bicuspid aortic valve is a condition wherein two of the aortic valvular leaflets fuse, resulting in a bicuspid valve, as opposed to the normal tricuspid aortic valve. Complications arising from bicuspid aortic valve range from a heart murmur to aortic stenosis or even aortic regurgitation. Bicuspid valve is a condition often associated with Marfan Syndrome and, as such, it is herein considered a Marfan-related disorder.

Ectopia Lentis (Dislocated Lens)

Ectopia lentis is a Marfan-related disorder wherein the eye's crystalline lens is displaced from its normal location. Ectopia lentis may have a variety of causes, but it is inherited at a higher frequency among Marfan sufferers. A partial dislocation may also be referred to as lens subluxation while a complete dislocation may also be referred to as lens luxation. Ectopia lentis may result in several difficulties including nearsightedness, astigmatism (irregular curvature of the eye), and fluctuated or blurred vision.

Mitral Valve Prolapse Syndrome

Mitral valve prolapse is characterized by the displacement of an abnormally thickened mitral valve leaflet into the left atrium during systole. While mitral valve prolapse may vary significantly in severity, severe forms may result in mitral regurgitation, congestive heart failure, and even cardiac arrest. For reasons that are not yet clear, mitral valve prolapse is more common in Marfan sufferers than in the general population, this it is herein considered a Marfan-related disorder.

Angiotensin (1-7) Peptides

As used herein, the term "angiotensin (1-7) peptide" refers to both naturally-occurring Angiotensin (1-7) and any functional equivalent, analogue or derivative of naturally-occurring Angiotensin (1-7). As used herein, "peptide" and "polypeptide" are interchangeable terms and refer to two or more amino acids bound together by a peptide bond. As used herein, the terms "peptide" and "polypeptide" include both linear and cyclic peptide. The terms "angiotensin-(1-7)", "Angiotensin-(1-7)", and "Ang-(1-7)" are used interchangeably.

Naturally-Occurring Angiotensin (1-7)

Naturally-occurring Angiotensin (1-7) (also referred to as Ang-(1-7)) is a seven amino acid peptide shown below:

(SEQ ID NO: 1)
$Asp^1-Arg^2-Val^3-Tyr^4-Ile^5-His^6-Pro^7$

It is part of the renin-angiotensin system and is converted from a precursor, also known as Angiotensinogen, which is an α-2-globulin that is produced constitutively and released into the circulation mainly by the liver. Angiotensinogen is a member of the serpin family and also known as renin substrate. Human angiotensinogen is 452 amino acids long, but other species have angiotensinogen of varying sizes. Typically, the first 12 amino acids are the most important for angiotensin activity:

(SEQ ID NO: 3)
$Asp^1-Arg^2-Val^3-Tyr^4-Ile^5-His^6-Pro^7-Phe^8-His^9-Leu^{10}-Val^{11}-Ile^{12}$

Different types of angiotensin may be formed by the action of various enzymes. For example, Angiotensin (1-7) is generated by action of Angiotensin-converting enzyme 2 (ACE 2).

Ang-(1-7) is an endogenous ligand for Mas receptors. Mas receptors are G-protein coupled receptor containing seven transmembrane spanning regions. As used herein, the term "angiotensin-(1-7) receptor" encompasses the G Protein-Coupled Mas Receptors.

As used herein, the term "naturally-occurring Angiotensin (1-7)" includes any Angiotensin (1-7) peptide purified from natural sources and any recombinantly produced or chemically synthesized peptides that have an amino acid sequence identical to that of the naturally-occurring Angiotensin (1-7).

Functional Equivalents, Analogs or Derivatives of Ang-(1-7)

In some embodiments, an angiotensin (1-7) peptide suitable for the present invention is a functional equivalent of naturally-occurring Ang-(1-7). As used herein, a functional equivalent of naturally-occurring Ang-(1-7) refers to any peptide that shares amino acid sequence identity to the naturally-occurring Ang-(1-7) and retain substantially the same or similar activity as the naturally-occurring Ang-(1-7). For example, in some embodiments, a functional equivalent of naturally-occurring Ang-(1-7) described herein has pro-angiogenic activity as determined using methods described herein or known in the art, or an activity such as nitric oxide release, vasodilation, improved endothelial function, antidiuresis, or one of the other properties discussed herein, that positively impacts angiogenesis. In some embodiments, a functional equivalent of naturally-occurring Ang-(1-7) described herein can bind to or activate an angiotensin-(1-7) receptor (e.g., the G protein-coupled Mas receptor) as determined using various assays described herein or known in the art. In some embodiments, a functional equivalent of Ang-(1-7) is also referred to as an angiotensin (1-7) analogue or derivative, or functional derivative.

Typically, a functional equivalent of angiotensin (1-7) shares amino acid sequence similarity to the naturally-occurring Ang-(1-7). In some embodiments, a functional equivalent of Ang-(1-7) according to the invention contains a sequence that includes at least 3 (e.g., at least 4, at least 5, at least 6, at least 7) amino acids from the seven amino acids that appear in the naturally-occurring Ang-(1-7), wherein the at least 3 (e.g., at least 4, at least 5, at least 6, or at least 7) amino acids maintain their relative positions and/or spacing as they appear in the naturally-occurring Ang-(1-7).

In some embodiments, a functional equivalent of angiotensin (1-7) also encompass any peptide that contain a sequence at least 50% (e.g., at least 60%, 70%, 80%, or 90%) identical to the amino acid sequence of naturally-occurring Ang-(1-7). Percentage of amino acid sequence identity can be determined by alignment of amino acid sequences. Alignment of amino acid sequences can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., Methods in Enzymology 266, 460-480 (1996); http://blast.wustl/edu/blast/README.html). WU-BLAST-2 uses several search parameters, most of which are set to the default values. The adjustable parameters are set with the following values: overlap span=1, overlap fraction=0.125, word threshold (T)=11. HSP score (S) and HSP S2 parameters are dynamic values and are established by the program itself, depending upon the composition of the particular sequence, however, the minimum values may be adjusted and are set as indicated above.

In some embodiments, a functional equivalent, analogue or derivative of Ang-(1-7) is a fragment of the naturally-occurring Ang-(1-7). In some embodiments, a functional equivalent, analogue or derivative of Ang-(1-7) contains amino acid substitutions, deletions and/or insertions in the naturally-occurring Ang-(1-7). Ang-(1-7) functional equivalents, analogues or derivatives can be made by altering the amino acid sequences by substitutions, additions, and/or deletions. For example, one or more amino acid residues within the sequence of the naturally-occurring Ang-(1-7) (SEQ ID NO:1) can be substituted by another amino acid of a similar polarity, which acts as a functional equivalent, resulting in a silent alteration. Substitution for an amino acid within the sequence may be selected from other members of the class to which the amino acid belongs. For example, the positively charged (basic) amino acids include arginine, lysine, and histidine. The nonpolar (hydrophobic) amino acids include leucine, isoleucine, alanine, phenylalanine, valine, proline, tryptophane, and methionine. The uncharged polar amino acids include serine, threonine, cysteine, tyrosine, asparagine, and glutamine. The negatively charged (acid) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions. For example, the amino acid sequence of a peptide inhibitor can be modified or substituted.

Examples of Ang-(1-7) functional equivalents, analogues and derivatives are described in the section entitled "Exemplary Angiotensin(1-7) Peptides" below.

An angiotensin-(1-7) peptide can be of any length. In some embodiments, an angiotensin-(1-7) peptide according to the present invention can contain, for example, from 4-25 amino acids (e.g., 4-20, 4-15, 4-14, 4-13, 4-12, 4-11, 4-10, 4-9, 4-8, 4-7 amino acids). In some embodiments, the linear peptide contains 4, 5, 6, 7, 8, 9, 10, 11, 12, 13, 14, 16, 17, 18, 19, 20, 21, 22, 23, 24, or 25 amino acids.

In some embodiments, an angiotensin-(1-7) peptide contains one or more modifications to increase protease resistance, serum stability and/or bioavailability. In some embodiments, suitable modifications are selected from pegylation, acetylation, glycosylation, biotinylation, substitution with D-amino acid and/or un-natural amino acid, and/or cyclization of the peptide.

As used herein, the term "amino acid," in its broadest sense, refers to any compound and/or substance that can be incorporated into a polypeptide chain. In certain embodiments, an amino acid has the general structure $H_2N$—$C(H)(R)$—$COOH$. In certain embodiments, an amino acid is a naturally-occurring amino acid. In certain embodiments, an amino acid is a synthetic or un-natural amino acid (e.g., $\alpha,\alpha$-disubstituted amino acids, N-alkyl amino acids); in some embodiments, an amino acid is a d-amino acid; in certain embodiments, an amino acid is an l-amino acid. "Standard amino acid" refers to any of the twenty standard amino acids commonly found in naturally occurring peptides including both l- and d-amino acids which are both incorporated in peptides in nature. "Nonstandard" or "unconventional amino acid" refers to any amino acid, other than the standard amino acids, regardless of whether it is prepared synthetically or obtained from a natural source. As used herein, "synthetic or un-natural amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical groups that can change the peptide's circulating half-life without adversely affecting its activity. Examples of unconventional or un-natural amino acids include, but are not limited to, citrulline, ornithine, norleucine, norvaline, 4-(E)-butenyl-4 (R)-methyl-N-methylthreonine (MeBmt), N-methyl-leucine (MeLeu), aminoisobutyric acid, statine, and N-methyl-alanine (MeAla). Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

In certain embodiments, angiotensin-(1-7) peptides contain one or more L-amino acids, D-amino acids, and/or un-natural amino acids.

In addition to peptides containing only naturally occurring amino acids, peptidomimetics or peptide analogs are also encompassed by the present invention. Peptide analogs are commonly used in the pharmaceutical industry as non-peptide drugs with properties analogous to those of the template peptide. The non-peptide compounds are termed "peptide mimetics" or peptidomimetics (Fauchere et al., *Infect. Immun.* 54:283-287 (1986); Evans et al., *J. Med. Chem.* 30:1229-1239 (1987)). Peptide mimetics that are structurally related to therapeutically useful peptides and may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as —$CH_2NH$—, —$CH_2S$—, —$CH_2$—$CH_2$—, —$CH=CH$— (cis and trans), —$CH_2SO$—, —$CH(OH)CH_2$—, —$COCH_2$— etc., by methods well known in the art (Spatola, Peptide Backbone Modifications, Vega Data, 1(3):267 (1983); Spatola et al. *Life Sci.* 38:1243-1249 (1986); Hudson et al. *Int. J. Pept. Res.* 14:177-185 (1979); and Weinstein. B., 1983, Chemistry and Biochemistry, of Amino Acids, Peptides and Proteins, Weinstein eds, Marcel Dekker, New-York,). Such peptide mimetics may have significant advantages over naturally-occurring polypeptides including more economical production, greater chemical stability, enhanced pharmacological properties (e.g., half-life, absorption, potency, efficiency, etc.), reduced antigenicity and others.

Ang-(1-7) peptides also include other types of peptide derivatives containing additional chemical moieties not normally part of the peptide, provided that the derivative retains the desired functional activity of the peptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives; (5) derivatives conjugated to an antibody or other biological ligand and other types of derivatives; and (6) derivatives conjugated to a polyethylene glycol (PEG) chain.

Ang-(1-7) peptides may be obtained by any method of peptide synthesis known to those skilled in the art, including synthetic (e.g., exclusive solid phase synthesis, partial solid phase synthesis, fragment condensation, classical solution synthesis, native-chemical ligation) and recombinant techniques. For example, the peptides or peptides derivatives can be obtained by solid phase peptide synthesis, which in brief, consist of coupling the carboxyl group of the C-terminal amino acid to a resin (e.g., benzhydrylamine resin, chloromethylated resin, hydroxymethyl resin) and successively adding N-alpha protected amino acids. The protecting groups may be any such groups known in the art. Before each new amino acid is added to the growing chain, the protecting group of the previous amino acid added to the chain is removed. Such solid phase synthesis has been disclosed, for example, by Merrifield, *J. Am. Chem. Soc.* 85: 2149 (1964); Vale et al., *Science* 213:1394-1397 (1981), in U.S. Pat. Nos. 4,305,872 and 4,316, 891, Bodonsky et al. *Chem. Ind.* (London), 38:1597 (1966); and Pietta and Marshall, *Chem. Comm.* 650 (1970) by techniques reviewed in Lubell et al. "Peptides" Science of Synthesis 21.11, *Chemistry of Amides.* Thieme, Stuttgart, 713-809 (2005). The coupling of amino acids to appropriate resins is also well known in the art and has been disclosed in U.S. Pat. No. 4,244,946. (Reviewed in Houver-Weyl, *Methods of Organic Chemistry*. Vol E22a. Synthesis of Peptides and Peptidomimetics, Murray Goodman, Editor-in-Chief, Thieme. Stuttgart. New York 2002).

Unless defined otherwise, the scientific and technological terms and nomenclature used herein have the same meaning as commonly understood by a person of ordinary skill to which this invention pertains. Generally, the procedures of cell cultures, infection, molecular biology methods and the like are common methods used in the art. Such standard techniques can be found in reference manuals such as, for example, Ausubel et al., *Current Protocols in Molecular Biology*, Wiley Interscience, New York, 2001; and Sambrook et al., *Molecular Cloning: A Laboratory Manual*, 3$^{rd}$ edition, Cold Spring Harbor Laboratory Press, N.Y., 2001.

During any process of the preparation of an Ang-(1-7) peptide, it may be desirable to protect sensitive reactive groups on any of the molecule concerned. This may be achieved by means of conventional protecting groups such as those described in Protective Groups In Organic Synthesis by T. W. Greene & P. G. M. Wuts, 1991, John Wiley and Sons, New-York; and Peptides: chemistry and Biology by Sewald and Jakubke, 2002, Wiley-VCH, Wheinheim p. 142. For example, alpha amino protecting groups include acyl type protecting groups (e.g., trifluoroacetyl, formyl, acetyl), aliphatic urethane protecting groups (e.g., t-butyloxycarbonyl (BOC), cyclohexyloxycarbonyl), aromatic urethane type protecting groups (e.g., fluorenyl-9-methoxy-carbonyl (Fmoc), benzyloxycarbonyl (Cbz), Cbz derivatives) and alkyl type protecting groups (e.g., triphenyl methyl, benzyl). The amino acids side chain protecting groups include benzyl (for Thr and Ser), Cbz (Tyr, Thr, Ser, Arg, Lys), methyl ethyl, cyclohexyl (Asp, His), Boc (Arg, His, Cys) etc. The protecting groups may be removed at a convenient subsequent stage using methods known in the art.

Further, Ang-(1-7) peptides may be synthesized according to the FMOC protocol in an organic phase with protective groups. Desirably, the peptides are purified with a yield of 70% with high-pressure liquid chromatography (HPLC) on a C18 chromatography column and eluted with an acetonitrile gradient of 10-60%. The molecular weight of a peptide can be verified by mass spectrometry (reviewed in Fields, G. B. "Solid-Phase Peptide Synthesis" *Methods in Enzymology*. Vol. 289, Academic Press, 1997).

Alternatively, Ang-(1-7) peptides may be prepared in recombinant systems using, for example, polynucleotide sequences encoding the polypeptides. It is understood that a polypeptide may contain more than one of the above-described modifications within the same polypeptide.

While peptides may be effective in eliciting a biological activity in vitro, their effectiveness in vivo might be reduced by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the peptide and require a free N-terminus (Powell et al., *Pharm. Res.* 10:1268-1273 (1993)). In light of this, it is often advantageous to use modified versions of peptides. The modified peptides retain the structural characteristics of the original L-amino acid peptides that confer the desired biological activity of Ang-(1-7) but are advantageously not readily susceptible to cleavage by protease and/or exopeptidases.

Systematic substitution of one or more amino acids of a consensus sequence with D-amino acid of the same type (e.g., D-lysine in place of L-lysine) may be used to generate more stable peptides. Thus, a peptide derivative or peptidomimetic of the present invention may be all L, all D or mixed D, L peptide, in either forward or reverse order. The presence of an N-terminal or C-terminal D-amino acid increases the in vivo stability of a peptide since peptidases cannot utilize a D-amino acid as a substrate (Powell et al., *Pharm. Res.* 10:1268-1273 (1993)). Reverse-D peptides are peptides containing D-amino acids, arranged in a reverse sequence relative to a peptide containing L-amino acids. Thus, the C-terminal residue of an L-amino acid peptide becomes N-terminal for the D-amino acid peptide, and so forth. Reverse D-peptides retain the same secondary conformation and therefore similar activity, as the L-amino acid peptides, but are more resistant to enzymatic degradation in vitro and in vivo, and thus can have greater therapeutic efficacy than the original peptide (Brady and Dodson, *Nature* 368:692-693 (1994); ameson et al., *Nature* 368:744-746 (1994)). Similarly, a reverse-L peptide may be generated using standard methods where the C-terminus of the parent peptide becomes takes the place of the N-terminus of the reverse-L peptide. It is contemplated that reverse L-peptides of L-amino acid peptides that do not have significant secondary structure (e.g., short peptides) retain the same spacing and conformation of the side chains of the L-amino acid peptide and therefore often have the similar activity as the original L-amino acid peptide. Moreover, a reverse peptide may contain a combination of L- and D-amino acids. The spacing between amino acids and the conformation of the side chains may be retained resulting in similar activity as the original L-amino acid peptide.

Another effective approach to confer resistance to peptidases acting on the N-terminal or C-terminal residues of a peptide is to add chemical groups at the peptide termini, such that the modified peptide is no longer a substrate for the peptidase. One such chemical modification is glycosylation of the peptides at either or both termini. Certain chemical modifications, in particular N-terminal glycosylation, have been shown to increase the stability of peptides in human serum (Powell et al., *Pharm. Res.* 10:1268-1273 (1993)). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified peptides consisting of peptides bearing an N-terminal acetyl group and/or a C-terminal amide group.

Substitution of non-naturally-occurring amino acids for natural amino acids in a subsequence of the peptides can also confer resistance to proteolysis. Such a substitution can, for instance, confer resistance to proteolysis by exopeptidases acting on the N-terminus without affecting biological activity. Examples of non-naturally-occurring amino acids include α,α-disubstituted amino acids, N-alkyl amino acids, C-α-methyl amino acids, β-amino acids, and β-methyl amino acids. Amino acids analogs useful in the present invention may include, but are not limited to, β-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formylmethionine, 3-methylhistidine and other unconventional amino acids. Furthermore, the synthesis of peptides with non-naturally-occurring amino acids is routine in the art.

In addition, constrained peptides comprising a consensus sequence or a substantially identical consensus sequence variation may be generated by methods well known in the art (Rizo and Gierasch, *Ann. Rev. Biochem.* 61:387-418 (1992)). For example, constrained peptides may be generated by adding cysteine residues capable of forming disulfide bridges and, thereby, resulting in a cyclic peptide. Cyclic peptides can be constructed to have no free N- or C-termini. Accordingly, they are not susceptible to proteolysis by exopeptidases, although they may be susceptible to endopeptidases, which do not cleave at peptide termini. The amino acid sequences of the peptides with N-terminal or C-terminal D-amino acids and of the cyclic peptides are usually identical to the sequences of the peptides to which they correspond, except for the presence of N-terminal or C-terminal D-amino acid residue, or their circular structure, respectively.

Cyclic Peptides

In some embodiments, a functional equivalent, analogue or derivative of naturally-occurring Ang-(1-7) is a cyclic peptide. As used herein, a cyclic peptide has an intramolecular covalent bond between two non-adjacent residues. The intramolecular bond may be a backbone to backbone, side-chain to backbone or side-chain to side-chain bond (i.e., terminal functional groups of a linear peptide and/or side-chain functional groups of a terminal or interior residue may be linked to achieve cyclization). Typical intramolecular bonds include disulfide, amide and thioether bonds. A variety of means for cyclizing polypeptides are well known in the art, as are many other modifications that can be made to such peptides. For a general discussion, see International Patent Publication Nos. WO 01/53331 and WO 98/02452, the contents of which are incorporated herein by reference. Such cyclic bonds and other modifications can also be applied to the cyclic peptides and derivative compounds of this invention.

Cyclic peptides as described herein may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. Cyclic peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Suitable derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Within further embodiments, cyclization may be achieved by amide bond formation. For example, a peptide bond may be formed between terminal functional groups (i.e., the amino and carboxy termini of a linear peptide prior to cyclization). Within another such embodiment, the linear peptide comprises a D-amino acid. Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate. Methods for forming amide bonds are generally well known in the art. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. Alternatively, cyclization can be performed using the azide method, in which a reactive azide intermediate is generated from an alkyl ester via a hydrazide. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF.

Exemplary Angiotensin-(1-7) Peptides

In certain aspects, the invention provides linear angiotensin-(1-7) peptides. As discussed above, the structure of naturally-occurring Ang-(1-7) is as follows:

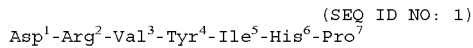

(SEQ ID NO: 1)
Asp$^1$-Arg$^2$-Val$^3$-Tyr$^4$-Ile$^5$-His$^6$-Pro$^7$

The peptides and peptide analogs of the invention can be generally represented by the following sequence:

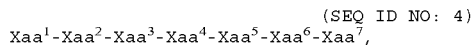

(SEQ ID NO: 4)
Xaa$^1$-Xaa$^2$-Xaa$^3$-Xaa$^4$-Xaa$^5$-Xaa$^6$-Xaa$^7$, or a pharmaceutically acceptable salt thereof.

Xaa$^1$ is any amino acid or a dicarboxylic acid. In certain embodiments, Xaa$^1$ is Asp, Glu, Asn, Acpc (1-aminocyclopentane carboxylic acid), Ala, Me$_2$Gly (N,N-dimethylglycine), Pro, Bet (betaine, 1-carboxy-N,N,N-trimethylmethanaminium hydroxide), Glu, Gly, Asp, Sar (sarcosine) or Suc (succinic acid). In certain such embodiments, Xaa$^1$ is a negatively-charged amino acid, such as Asp or Glu, typically Asp.

Xaa$^2$ is Arg, Lys, Ala, Cit (citrulline), Orn (ornithine), acetylated Ser, Sar, D-Arg and D-Lys. In certain embodiments, Xaa$^2$ is a positively-charged amino acid such as Arg or Lys, typically Arg.

Xaa$^3$ is Val, Ala, Leu, Nle (norleucine), Ile, Gly, Lys, Pro, HydroxyPro (hydroxyproline), Aib (2-aminoisobutyric acid), Acpc or Tyr. In certain embodiments, Xaa$^3$ is an aliphatic amino acid such as Val, Leu, Ile or Nle, typically Val or Nle.

Xaa$^4$ is Tyr, Tyr(PO$_3$), Thr, Ser, homoSer (homoserine), azaTyr (aza-α$^1$-homo-L-tyrosine) or Ala. In certain embodiments, Xaa$^4$ is a hydroxyl-substituted amino acid such as Tyr, Ser or Thr, typically Tyr.

Xaa$^5$ is Ile, Ala, Leu, norLeu, Val or Gly. In certain embodiments, Xaa$^5$ is an aliphatic amino acid such as Val, Leu, Ile or Nle, typically Ile.

Xaa$^6$ is His, Arg or 6-NH$_2$-Phe (6-aminophenylalaine). In certain embodiments, Xaa$^6$ is a fully or partially positively-charged amino acid such as Arg or His.

Xaa$^7$ is Cys, Pro or Ala.

In certain embodiments, one or more of Xaa$^1$-Xaa$^7$ is identical to the corresponding amino acid in naturally-occurring Ang-(1-7). In certain such embodiments, all but one or two of Xaa$^1$-Xaa$^1$ are identical to the corresponding amino acid in naturally-occurring Ang-(1-7). In other embodiments, all of Xaa$^1$-Xaa$^6$ are identical to the corresponding amino acid in naturally-occurring Ang-(1-7).

In certain embodiments, Xaa$^3$ is Nle. When Xaa$^3$ is Nle, one or more of Xaa$^1$-Xaa$^2$ and Xaa$^{4-7}$ are optionally identical to the corresponding amino acid in naturally-occurring Ang-(1-7). In certain such embodiments, all but one or two of Xaa$^1$-Xaa$^2$ and Xaa$^{4-7}$ are identical to the corresponding amino acid in naturally-occurring Ang-(1-7). In other embodiments, all of Xaa$^1$-Xaa$^2$ and Xaa$^{4-7}$ are identical to the corresponding amino acid in naturally-occurring Ang-(1-7), resulting in the amino acid sequence: Asp$^1$-Arg$^2$-Nle$^3$-Tyr$^4$-Ile$^5$-His$^6$-Pro$^7$ (SEQ ID NO:5).

In certain embodiments, the peptide has the amino acid sequence Asp$^1$-Arg$^2$-Val$^3$-Ser$^4$-Ile$^5$-His$^6$-Cys$^7$ (SEQ ID NO:2) or Asp$^1$-Arg$^2$-Val$^3$-ser$^4$-Ile$^5$-His$^6$-Cys$^7$ (SEQ ID NO:6).

In some embodiments, a linear angiotensin (1-7) peptide is an Ang (1-9) peptide having a sequence of Asp$^1$-Arg$^2$-Val$^3$-Tyr$^4$-Ile$^5$-His$^6$-Pro$^7$-Phe$^8$-His$^9$ (SEQ ID NO: 23). In some embodiments, an angiotensin (1-7) peptide is a derivative of Ang (1-9). For exemplary Ang (1-9) peptides, including Ang (1-9) derivatives, see U.S. Patent Publication 2012/0172301, the disclosure of which is hereby incorporated by reference.

In some embodiments, a linear angiotensin (1-7) peptide is Alamandine, or an Alamandine derivative. Alamandine is a naturally occurring peptide with an amino acid sequence of Ala'-Arg$^2$-Val$^3$-Tyr$^4$-Ile$^5$-His$^6$-Pro'(SEQ ID NO: 24) that is known to be a component of the Renin-Angiotensin system (see Lautner et al., Discovery and Characterization of Alamandine, 2013, *Circ. Res.* 112(8): 1104-1111). A discussion of Alamandine and Alamandine derivatives may be found in European Patent Application 2,264,048, the disclosure of which is hereby incorporated by reference.

Exemplary Cyclic Angiotensin (1-7) Peptides

In certain aspects, the invention provides a cyclic angiotensin-(1-7) (Ang-(1-7)) peptide analog comprising a linkage, such as between the side chains of amino acids corresponding to positions Tyr$^4$ and Pro$^7$ in Ang. These peptide analogs typically comprise 7 amino acid residues, but can also include a cleavable sequence. As discussed in greater detail below, the invention includes fragments and analogs where one or more amino acids are substituted by another amino acid (including fragments). One example of such an analog is Asp$^1$-Arg$^2$-Val$^3$-Ser$^4$-Ile$^5$-His$^6$-Cys$^7$ (SEQ ID NO: 22), wherein a linkage is formed between Ser$^4$ and Cys$^7$.

Although the following section describes aspects of the invention in terms of a thioether bond linking residues at the 4- and 7-positions, it should be understood that other linkages (as described above) could replace the thioether bridge and that other residues could be cyclized. A thioether bridge is also referred to as a monosulfide bridge or, in the case of Ala-S-Ala, as a lanthionine bridge. Thioether bridge-containing peptides can be formed by two amino acids having one of the following formulas:

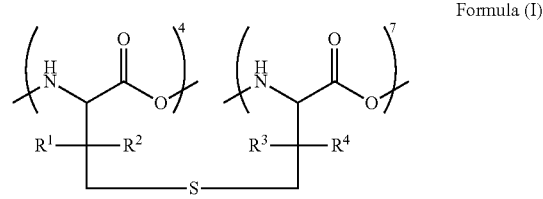

Formula (I)

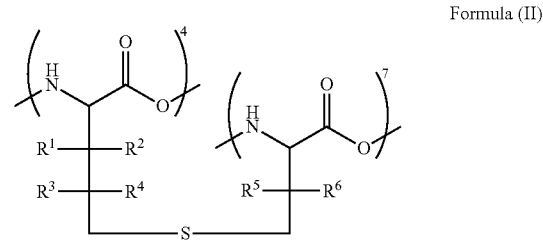

Formula (II)

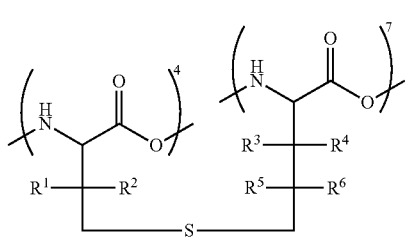

Formula (III)

In these formulae, $R^1$, $R^2$, $R^3$, $R^4$, $R^5$ and $R^6$ are independently —H, an alkyl (e.g., $C_1$-$C_6$ alkyl, $C_1$-$C_4$ alkyl) or an aralkyl group, where the alkyl and aralkyl groups are optionally substituted with one or more halogen, —OH or —NRR' groups (where R and R' are independently —H or $C_1$-$C_4$ alkyl). In certain embodiments, $R^1$, $R^2$, $R^3$, $R^4$, $R^5$ and $R^6$ are each independently —H or —$CH_3$, such where all are —H.

In certain embodiments, the invention provides an Ang analog or derivative comprising a thioether bridge according to formula (I). Typically, $R^1$, $R^2$, $R^3$ and $R^4$ are independently selected from —H and —$CH_3$. Peptides comprising a thioether bridge according to formula (I) can be produced, for example, by lantibiotic enzymes or by sulfur extrusion of a disulfide. In one example, the disulfide from which the sulfur is extruded can be formed by D-cysteine in position 4 and L-cysteine in position 7 or by D-cysteine in position 4 and L-penicillamine in position 7 (see, e.g., Galande, Trent and Spatola (2003) *Biopolymers* 71, 534-551).

In other embodiments, the linkage of the two amino acids can be the bridges depicted in Formula (II) or Formula (III). Peptides comprising a thioether bridge according to Formula (II) can be made, for example, by sulfur extrusion of a disulfide formed by D-homocysteine in position 4 and L-cysteine in position 7. Similarly, peptides comprising a thioether bridge as in Formula (III) can be made, for example, by sulfur extrusion of a disulfide formed by D-cysteine in position 4 and L-homocysteine in position 7.

As discussed above, the Ang analogs and derivatives of the invention vary in length and amino acid composition. The Ang analogs and derivatives of the invention preferably have biological activity or are an inactive precursor molecule that can be proteolytically activated (such as how angiotensin(I), with 10 amino acids, is converted to active fragments by cleavage of 2 amino acids). The size of an Ang analog or derivative can vary but is typically between from about 5 to 10 amino acids, as long as the "core" pentameric segment comprising the 3-7 Nle-thioether-ring structure is encompassed. The amino acid sequence of an analog or derivative of the invention can vary, typically provided that it is biologically active or can become proteolytically activated. Biological activity of an analog or derivative can be determined using methods known in the art, including radioligand binding studies, in vitro cell activation assays and in vivo experiments. See, for example, Godeny and Sayeski, (2006) *Am. J. Physiol. Cell. Physiol.* 291:C1297-1307; Sarr et al., *Cardiovasc. Res.* (2006) 71:794-802; and Koziarz et al., (1933) *Gen. Pharmacol.* 24:705-713.

Ang analogs and derivatives where only the length of the peptide is varied include the following:

a 4,7-cyclized analog designated [$Cyc^{4-7}$]Ang-(1-7), which is derived from natural Ang-(1-7) ($Asp^1$-$Arg^2$-$Val^3$-$Cyc^4$-$Ile^5$-$His^6$-$Cyc^7$, SEQ ID NO:7).

a 4,7-cyclized analog designated [$Nle^3$, $Cyc^{4-7}$]Ang-(1-10), which is derived from natural Angiotensin I (Ang-(1-10)) ($Asp^1$-$Arg^2$-$Nle^3$-$Cyc^4$-$Ile^5$-$His^6$-$Cyc^7$-$Phe^8$-$His^9$-$Leu^{10}$, SEQ ID NO:8);

a 4,7-cyclized analog designated [$Nle^3$, $Cyc^{4-7}$]Ang-(1-8), which is derived from natural Angiotensin II (Ang-(1-8)) ($Asp^1$-$Arg^2$-$Nle^3$-$Cyc^4$-$Ile^5$-$His^6$-$Cyc^7$-$Phe^8$, SEQ ID NO:9);

a 4,7-cyclised analog designated [$Nle^3$, $Cyc^{4-7}$]Ang-(2-8), which is derived from natural Angiotensin III (Ang-(2-8)) ($Arg^2$-$Nle^3$-$Cyc^4$-$Ile^5$-$His^6$-$Cyc^7$-$Phe^8$, SEQ ID NO:10);

a 4,7-cyclised analog designated [$Nle^3$, $Cyc^{4-7}$]Ang-(3-8), which is derived from natural Angiotensin IV (Ang-(3-8)) ($Nle^3$-$Cyc^4$-$Ile^5$-$His^6$-$Cyc^7$-$Phe^8$, SEQ ID NO:11);

a 4,7-cyclised analog designated [$Nle^3$, $Cyc^{4-7}$]Ang-(1-7) derived from natural Ang-(1-7) ($Asp^1$-$Arg^2$-$Nle^3$-$Cyc^4$-$Ile^5$-$His^6$-$Cyc^7$, SEQ ID NO:12); and a 4,7-cyclised analog designated [$Nle^3$, $Cyc^{4-7}$]Ang-(1-9) derived from natural Ang-(1-9) ($Asp^1$-$Arg^2$-$Nle^3$-$Cyc^4$-$Ile^5$-$His^6$-$Cyc^7$-$Phe^8$-$His^9$, SEQ ID NO:13).

These analogs can have one of the thioether bridges shown in Formulae (I)-(III) as the $Cyc^{4-7}$ moiety, for example, where $Cyc^4$ and $Cyc^7$ are represented by Formula (I), such as where $R^1$-$R^4$ are each —H or —$CH_3$, typically —H.

As compared to the amino acid sequence of the natural angiotensin peptide, the amino acids at positions 4 and 7 of the $Cyc^{4-7}$ analog are modified to allow introduction of the thioether-ring structures shown above. In addition to the length of the Ang analogs, the amino acids at positions other than 3, 4 and 7 can be the same or different from the naturally-occurring peptide, typically provided that the analog retains a biological function. For analogs of inactive precursors, like [$Cyc^{4-7}$]Ang-(1-10), biological function refers to one or both of an analog's susceptibility to angiotensin-converting enzymes that can cleave it to a biologically active fragment (e.g. Ang-(1-8) or Ang-(1-7)) or the biological activity of the fragment itself. In certain embodiments, an Ang analog or derivative of the invention has no intrinsic function but inhibits the effects of one or more naturally-occurring angiotensin compounds.

In certain embodiments, an Ang analog of the invention is represented by Formula (IV):

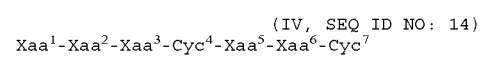

(IV, SEQ ID NO: 14)
$Xaa^1$-$Xaa^2$-$Xaa^3$-$Cyc^4$-$Xaa^5$-$Xaa^6$-$Cyc^7$ $Xaa^1$ is any amino acid, but typically a negatively-charged amino acid such as Glu or Asp, more typically Asp.

$Xaa^2$ is a positively-charged amino acid such as Arg or Lys, typically Arg.

$Xaa^3$ is an aliphatic amino acid, such as Leu, Ile or Val, typically Val.

$Cyc^4$ forms a thioether bridge in conjunction with $Cyc^7$. $Cyc^4$ can be a D-stereoisomer and/or a L-stereoisomer, typically a D-stereoisomer. Examples of $Cyc^4$ (taken with $Cyc^7$) are shown in Formulas (I), (II) and (III). Typically, the R groups in Formulae (I), (II) and (III) are —H or —$CH_3$, especially —H.

$Xaa^5$ is an aliphatic amino acid, such as Leu, Ile or Val, typically Ile.

$Xaa^6$ is His.

$Cyc^7$ forms a thioether bridge in conjunction with $Cyc^4$, such as in Formula (I), (II) or (III). $Cyc^7$ can be a D-stereoisomer and/or a L-stereoisomer, typically a L-stereoisomer. Examples of $Cyc^7$ (taken with $Cyc^4$) are shown in Formulas (I), (II), (III) and (IV). Typically, the R groups in Formulae (I), (II),) and (III) and (IV) are —H or —$CH_3$, especially —H.

In certain embodiments, one or more of $Xaa^1$-$Xaa^6$ (excluding $Cyc^4$ and $Cyc^7$) is identical to the corresponding amino acid in naturally-occurring Ang-(1-7). In certain such embodiments, all but one or two of Xaa¹-Xaa⁶ are identical to the corresponding amino acid in naturally-occurring Ang-(1-7). In other embodiments, all of Xaa¹-Xaa⁶ are identical to the corresponding amino acid in naturally-occurring Ang-(1-7).

In certain embodiments, Cyc⁴ and Cyc⁷ are independently selected from Abu (2-aminobutyric acid) and Ala (alanine), where Ala is present in at least one position. Thus, cyclic analogs can have a thioether linkage formed by -Ala⁴-S-Ala⁷- (Formula (I), where R¹-R⁴ are each —H); -Ala⁴-S-Abu⁷- (Formula (I): R¹-R³ are —H and R⁴ is —CH₃) or -Abu⁴-S-Ala⁷- (Formula (I): R¹, R³ and R⁴ are —H and R² is —CH₃). Specific examples of cyclic analogs comprise a -Abu⁴-S-Ala⁷- or -Ala⁴-S-Ala⁷-linkage.

In certain embodiments, the invention provides an Ang-(1-7) analog with a thioether-bridge between position 4 and position 7 having the amino acid sequence Asp¹-Arg²-Val³-Abu⁴-Ile⁵-His⁶-Ala⁷ (SEQ ID NO:15) or the amino acid sequence Asp¹-Arg²-Val³-Ala⁴-Ile⁵-His⁶-Ala⁷ (SEQ ID NO:16), which are represented by the following structural diagrams:

Cyc⁴ forms a thioether bridge in conjunction with Cyc⁷. Cyc⁴ can be a D-stereoisomer and/or a L-stereoisomer, typically a D-stereoisomer. Examples of Cyc⁴ (taken with Cyc⁷) are shown in Formulas (I), (II) and (III). Typically, the R groups in Formulae (I), (II) and (III) are —H or —CH₃, especially —H.

Xaa⁵ is an aliphatic amino acid, such as Leu, Nle, Ile or Val, typically Ile.

Xaa⁶ is His.

Cyc⁷ forms a thioether bridge in conjunction with Cyc⁴, such as in Formula (I), (II) or (III). Cyc⁷ can be a D-stereoisomer and/or a L-stereoisomer, typically a L-stereoisomer. Examples of Cyc⁷ (taken with Cyc⁴) are shown in Formulas (I), (II) and (III). Typically, the R groups in Formulae (I), (II) and (III) are —H or —CH₃, especially —H.

Xaa⁸, when present, is an amino acid other than Pro, typically Phe or Ile. In certain embodiments, Ile results in an inhibitor of Ang(1-8). In certain embodiments, Phe maintains the biological activity of Ang(1-8) or Ang(1-10).

Xaa⁹, when present, is His.

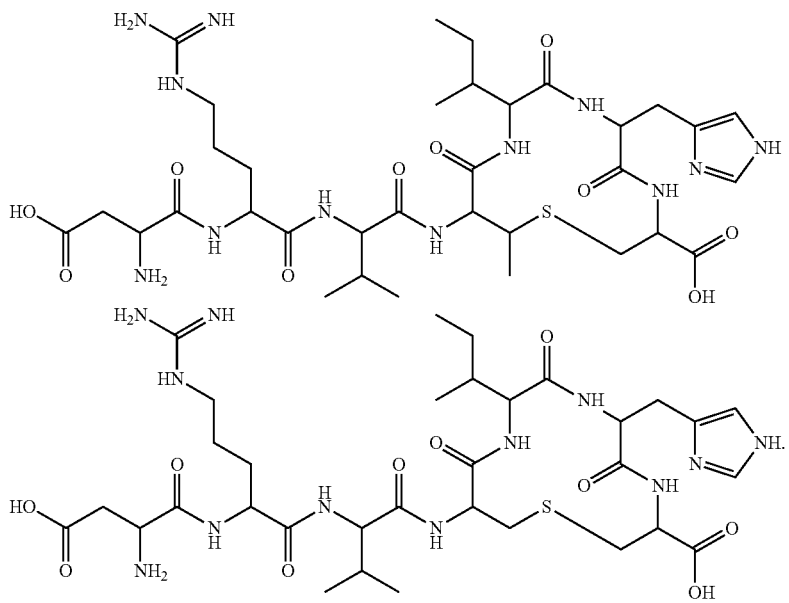

In certain embodiments, an Ang analog or derivative of the invention is represented by Formula (V):

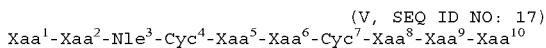

(V, SEQ ID NO: 17)
Xaa¹-Xaa²-Nle³-Cyc⁴-Xaa⁵-Xaa⁶-Cyc⁷-Xaa⁸-Xaa⁹-Xaa¹⁰

As discussed above, one or more of Xaa¹, Xaa², Xaa⁸, Xaa⁹ and Xaa¹⁰ are absent in certain embodiments. For example, (1) Xaa¹⁰ is absent, (2) Xaa⁹ and Xaa¹⁰ are absent, (3) Xaa⁸, Xaa⁹ and Xaa¹⁰ are absent, (4) Xaa¹ is absent, (5) Xaa¹ and Xaa¹⁰ are absent, (6) Xaa¹, Xaa⁹ and Xaa¹⁰ are absent, (7) Xaa¹, Xaa⁸, Xaa⁹ and Xaa¹⁰ are absent, (8) Xaa¹ and Xaa² are absent, (9) Xaa¹, Xaa² and Xaa¹⁰ are absent, (10) Xaa¹, Xaa², Xaa⁹ and Xaa¹⁰ are absent, or (11) Xaa¹, Xaa², Xaa⁸, Xaa⁹ and Xaa¹⁰ are absent. For each of these embodiments, the remaining amino acids have the values described below.

Xaa¹, when present, is any amino acid, but typically a negatively charged amino acid such as Glu or Asp, more typically Asp.

Xaa², when present, is a positively charged amino acid such as Arg or Lys, typically Arg.

Nle³ is norleucine.

Xaa¹⁰, when present, is an aliphatic residue, for example, Ile, Val or Leu, typically Leu.

In certain embodiments, one or more of Xaa¹-Xaa¹⁰ (excluding Nle³, Cyc⁴ and Cyc⁷) is identical to the corresponding amino acid in naturally-occurring Ang (including Ang-(1-7), Ang(1-8), Ang(1-9), Ang(1-10), Ang(2-7), Ang(2-8), Ang(2-9), Ang(2-10), Ang(3-8), Ang(3-9) and Ang(3-10). In certain such embodiments, all but one or two of Xaa¹-Xaa¹⁰ (for those present) are identical to the corresponding amino acid in naturally-occurring Ang. In other embodiments, all of Xaa¹-Xaa¹⁰ (for those present) are identical to the corresponding amino acid in naturally-occurring Ang.

In certain embodiments, Cyc⁴ and Cyc⁷ are independently selected from Abu (2-aminobutyric acid) and Ala (alanine), where Ala is present at at least one position. Thus, encompassed are cyclic analogs comprising a thioether linkage formed by -Ala⁴-S-Ala⁷- (Formula (I), where R¹-R⁴ are each —H); -Ala⁴-S-Abu⁷- (Formula (I): R¹-R³ are —H and R⁴ is —CH₃) or -Abu⁴-S-Ala⁷- (Formula (I): R¹, R³ and R⁴ are —H and R² is —CH₃). Specific cyclic analogs comprise a -Abu⁴-S-Ala'- or -Ala⁴-S-Ala⁷-linkage.

In particular, the invention provides an Ang-(1-7) analog or derivative with a thioether-bridge between position 4 and position 7 having the amino acid sequence Asp$^1$-Arg$^2$-Nle$^3$-Abu$^4$-Ile$^5$-His$^6$-Ala$^7$ (SEQ ID NO:18) or the amino acid sequence Asp$^1$-Arg$^2$-Nle$^3$-Ala$^4$-Ile$^5$-His$^6$-Ala$^7$ (SEQ ID NO:19).

In another aspect, the invention provides an Ang-(1-8) analog or derivative with a thioether-bridge between position 4 and position 7 having Ang-(1-8) antagonistic activity, in particular an Ang(1-8) analog or derivative having the amino acid sequence Asp$^1$-Arg$^2$-Nle$^3$-Abu$^4$-Ile$^5$-His$^6$-Ala$^7$-Ile$^8$ (SEQ ID NO:20), or the amino acid sequence Asp$^1$-Arg$^2$-Nle$^3$-Ala$^4$-Ile$^5$-His$^6$-Ala$^7$-Ile$^8$ (SEQ ID NO:21).

An alkyl group is a straight chained or branched non-aromatic hydrocarbon that is completely saturated. Typically, a straight chained or branched alkyl group has from 1 to about 20 carbon atoms, preferably from 1 to about 10. Examples of straight chained and branched alkyl groups include methyl, ethyl, n-propyl, iso-propyl, n-butyl, sec-butyl, tert-butyl, pentyl, hexyl, pentyl and octyl. A C1-C4 straight chained or branched alkyl group is also referred to as a "lower alkyl" group.

An aralkyl group is an alkyl group substituted by an aryl group. Aromatic (aryl) groups include carbocyclic aromatic groups such as phenyl, naphthyl, and anthracyl, and heteroaryl groups such as imidazolyl, thienyl, furyl, pyridyl, pyrimidyl, pyranyl, pyrazolyl, pyrrolyl, pyrazinyl, thiazolyl, oxazolyl, and tetrazolyl. Aromatic groups also include fused polycyclic aromatic ring systems in which a carbocyclic aromatic ring or heteroaryl ring is fused to one or more other heteroaryl rings. Examples include benzothienyl, benzofuryl, indolyl, quinolinyl, benzothiazole, benzoxazole, benzimidazole, quinolinyl, isoquinolinyl and isoindolyl.

Ang (1-7) Receptor Agonists

In some embodiments, the present invention provides methods of treating brain conditions including administering to a subject who is suffering from or susceptible to one or more brain conditions an angiotensin (1-7) receptor agonist. As used herein, the term "angiotensin-(1-7) receptor agonist" encompasses any molecule that has a positive impact in a function of an angiotensin-(1-7) receptor, in particular, the G-protein coupled Mas receptor. In some embodiments, an angiotensin-(1-7) receptor agonist directly or indirectly enhances, strengthens, activates and/or increases an angiotensin-(1-7) receptor (i.e., the Mas receptor) activity. In some embodiments, an angiotensin-(1-7) receptor agonist directly interacts with an angiotensin-(1-7) receptor (i.e., the Mas receptor). Such agonists can be peptidic or non-peptidic including, e.g., proteins, chemical compounds, small molecules, nucleic acids, antibodies, drugs, ligands, or other agents. In some embodiments, the angiotensin (1-7) receptor agonist is a non-peptidic agonist.

An exemplary class of angiotensin-(1-7) receptor agonists are 1-(p-thienylbenzyl)imidazoles. Examples of these non-peptide angiotensin-(1-7) receptor agonists are represented by Structural Formula (VI):

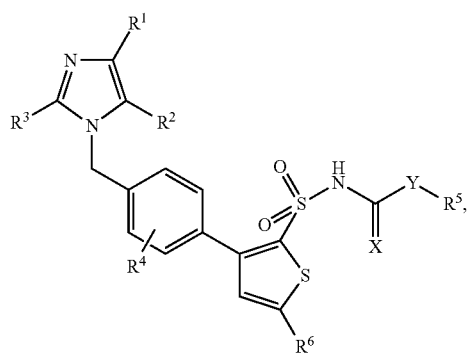

(VI)

or pharmaceutically acceptable salts thereof, wherein:

$R^1$ is halogen, hydroxyl, $(C_1$-$C_4)$-alkoxy, $(C_1$-$C_8)$-alkoxy wherein 1 to 6 carbon atoms are replaced by the heteroatoms O, S, or NH (preferably by O), $(C_1$-$C_4)$-alkoxy substituted by a saturated cyclic ether such as tetrahydropyran or tetrahydrofuran, O—$(C_1$-$C_4)$-alkenyl, O—$(C_1$-$C_4)$-alkylaryl, or aryloxy that is unsubstituted or substituted by a substituent selected from halogen, $(C_1$-$C_3)$-alkyl, $(C_1$-$C_3)$-alkoxy and trifluoromethyl;

$R^2$ is CHO, COOH, or (3) CO—O—$(C_1$-$C_4)$-alkyl;

$R^3$ is $(C_1$-$C_4)$-alkyl or aryl;

$R^4$ is hydrogen, halogen (chloro, bromo, fluoro), or $(C_1$-$C_4)$-alkyl;

X is oxygen or sulfur;

Y is oxygen or —NH—;

$R^5$ is hydrogen, $(C_1$-$C_6)$-alkyl; or $(C_1$-$C_4)$-alkylaryl, where $R^5$ is hydrogen when Y is —NH—; and $R^6$ is $(C_1$-$C_5)$-alkyl.

In certain embodiments, $R^1$ is not halogen when $R^2$ is COOH or CO—O—$(C_1$-$C_4)$-alkyl.

In some embodiments, an angiotensin-(1-7) receptor agonist is AVE 0991, 5-formyl-4-methoxy-2-phenyl-1 [[4-[2-(ethylaminocarbonylsulfonamido)-5-isobutyl-3-thienyl]-phenyl]-methyl]-imidazole, which is represented by the following structure:

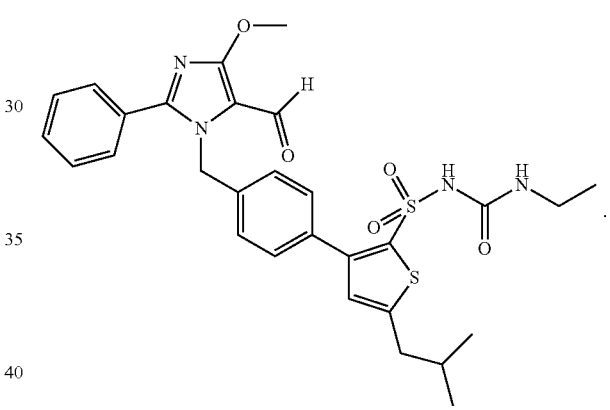

Another exemplary class of angiotensin-(1-7) receptor agonists are p-thienylbenzylamides. Examples of these non-peptide angiotensin-(1-7) receptor agonists are represented by Structural Formula (VII):

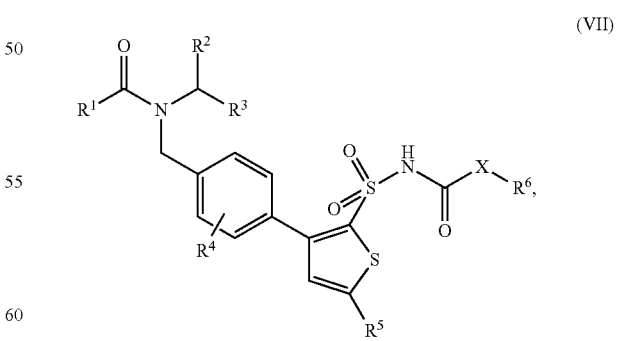

(VII)

or a pharmaceutically acceptable salt thereof, wherein:

$R^1$ is $(C_1$-$C_5)$-alkyl that is unsubstituted or substituted by a radical chosen from $NH_2$, halogen, O—$(C_1$-$C_3)$-alkyl, CO—O—$(C_1$-$C_3)$-alkyl and $CO_2H$, $(C_3$-$C_8)$-cycloalkyl, $(C_1$-$C_3)$-alkyl-$(C_3$-$C_8)$-cycloalkyl, $(C_6$-$C_{10})$-aryl that is unsubstituted or substituted by a radical chosen from halogen and O—($C_1$-$C_3$)-alkyl, ($C_1$-$C_3$)-alkyl-($C_6$-$C_{10}$)-aryl where the aryl radical is unsubstituted or substituted by a radical chosen from halogen and O—($C_1$-$C_3$)-alkyl, ($C_1$-$C_5$)-heteroaryl, or ($C_1$-$C_3$)-alkyl-($C_1$-$C_5$)-heteroaryl;

$R^2$ is hydrogen, ($C_1$-$C_6$)-alkyl that is unsubstituted or substituted by a radical chosen from halogen and O—($C_1$-$C_3$)-alkyl, ($C_3$-$C_8$)-cycloalkyl, ($C_1$-$C_3$)-alkyl-($C_3$-$C_8$)-cycloalkyl, ($C_6$-$C_{10}$)-aryl that is unsubstituted or substituted by a radical chosen from among halogen, O—($C_1$-$C_3$)-alkyl and CO—O—($C_1$-$C_3$)-alkyl, or ($C_1$-$C_3$)-alkyl-($C_6$-$C_{10}$)-aryl that is unsubstituted or substituted by a radical chosen from halogen and O—($C_1$-$C_3$)-alkyl;

$R^3$ is hydrogen, COOH, or COO—($C_1$-$C_4$)-alkyl;

$R^4$ is hydrogen, halogen; or ($C_1$-$C_4$)-alkyl;

$R^5$ is hydrogen or ($C_1$-$C_6$)-alkyl;

$R^6$ is hydrogen, ($C_1$-$C_6$)-alkyl, ($C_1$-$C_3$)-alkyl-($C_3$-$C_8$)-cycloalkyl, or ($C_2$-$C_6$)-alkenyl; and X is oxygen or NH.

Additional examples of angiotensin-(1-7) receptor agonists are described in U.S. Pat. No. 6,235,766, the contents of which are incorporated by reference herein.

Various angiotensin-(1-7) receptor agonists described above can be present as pharmaceutically acceptable salts. As used herein, "a pharmaceutically acceptable salt" refers to salts that retain the desired activity of the peptide or equivalent compound, but preferably do not detrimentally affect the activity of the peptide or other component of a system, which uses the peptide. Examples of such salts are acid addition salts formed with inorganic acids, for example, hydrochloric acid, hydrobromic acid, sulfuric acid, phosphoric acid, nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts formed from a cationic material may utilize the conjugate base of these inorganic and organic acids. Salts may also be formed with polyvalent metal cations such as zinc, calcium, bismuth, barium, magnesium, aluminum, copper, cobalt, nickel and the like or with an organic cation formed from N,N'-dibenzylethylenediamine or ethylenediamine, or combinations thereof (e.g., a zinc tannate salt). The non-toxic, physiologically acceptable salts are preferred.

The salts can be formed by conventional means such as by reacting the free acid or free base forms of the product with one or more equivalents of the appropriate acid or base in a solvent or medium in which the salt is insoluble, or in a solvent such as water which is then removed in vacuo or by freeze-drying, or by exchanging the cations of an existing salt for another cation on a suitable ion exchange resin.

An alkyl group is a straight chained or branched non-aromatic hydrocarbon that is completely saturated. Typically, a straight chained or branched alkyl group has from 1 to about 20 carbon atoms, preferably from 1 to about 10. Examples of straight chained and branched alkyl groups include methyl, ethyl, n-propyl, iso-propyl, n-butyl, sec-butyl, tert-butyl, pentyl, hexyl, pentyl and octyl. A C1-C4 straight chained or branched alkyl group is also referred to as a "lower alkyl" group.

An alkenyl group is a straight chained or branched non-aromatic hydrocarbon that includes one or more double bonds. Typically, a straight chained or branched alkenyl group has from 2 to about 20 carbon atoms, preferably from 2 to about 10. Examples of straight chained and branched alkenyl groups include ethenyl, n-propenyl, and n-butenyl.

Aromatic (aryl) groups include carbocyclic aromatic groups such as phenyl, naphthyl, and anthracyl, and heteroaryl groups such as imidazolyl, thienyl, furyl, pyridyl, pyrimidyl, pyranyl, pyrazolyl, pyrrolyl, pyrazinyl, thiazolyl, oxazolyl, and tetrazolyl. Aromatic groups also include fused polycyclic aromatic ring systems in which a carbocyclic aromatic ring or heteroaryl ring is fused to one or more other heteroaryl rings. Examples include benzothienyl, benzofuryl, indolyl, quinolinyl, benzothiazole, benzoxazole, benzimidazole, quinolinyl, isoquinolinyl and isoindolyl.

An aralkyl group is an alkyl group substituted by an aryl group.

Formulations

In accordance with the methods of the invention, an Ang (1-7) peptide or angiotensin (1-7) receptor agonist as described herein of the invention can be administered to a subject alone (e.g., as a purified peptide or compound), or as a component of a composition or medicament (e.g., in the manufacture of a medicament for the treatment of the disease), as described herein. The compositions can be formulated with a physiologically acceptable carrier or excipient to prepare a pharmaceutical composition. The carrier and composition can be sterile. The formulation should suit the mode of administration, for example intravenous or subcutaneous administration. Methods of formulating compositions are known in the art (see, e.g., Remington's Pharmaceuticals Sciences, 17$^{th}$ Edition, Mack Publishing Co., (Alfonso R. Gennaro, editor) (1989)).

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring and/or aromatic substances and the like) which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, sustained release formulation, or powder. The composition can also be formulated as a suppository, with traditional binders and carriers such as triglycerides.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

In some embodiments, provided compositions, including those provided as pharmaceutical formulations, comprise a liquid carrier such as but not limited to water, saline, phosphate buffered saline, Ringer's solution, dextrose solution, serum-containing solutions, Hank's solution, other aqueous physiologically balanced solutions, oils, esters and glycols.

An Ang (1-7) peptide or angiotensin (1-7) receptor agonist as described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Oral Formulations

In some embodiments, a suitable pharmaceutical composition is an oral formulation. It is contemplated that any medically-acceptable oral formulation may be used within the scope of the present invention.

In some embodiments, provided compositions include at least one pH-lowering agent. It is contemplated that a pH-lowering agent suitable for use in some embodiments of the present invention include any pharmaceutically acceptable pH-lowering agent, or combination of pH-lowering agents, that are a) not toxic to the gastrointestinal tract, b) are capable of either delivering hydrogen ions or capable of inducing higher hydrogen ion content from the local environment, and/or c) that are capable of being orally administered in an amount sufficient to lower the local intestinal pH below the pH optima for proteases found there. Various tests may be used to determine if a pH-lowering agent is suitable for the present invention and what amount is appropriate. For example, a pH-lowering agent or combination of pH-lowering agents is suitable for the present invention if a particular amount, when added to a solution of 10 milliliters of 0.1M sodium bicarbonate lowers the pH of the solution to no higher than 5.5, 4.7, or 3.5. In some embodiments, an amount of pH-lowering agent or agents may be added to lower pH, in a solution of 10 milliliters of 0.1M sodium bicarbonate, to no higher than 3.4, 3.2, 3.0, or 2.8.

In some embodiments, a suitable pH-lowering agent or agents include at least one pH-lowering agent that has a pKa no higher than 4.2 (e.g., no higher than 4.0, 3.8, 3.6, 3.4, 3.2, 3.0 or 2.8). Exemplary pH-lowering agents suitable for the present invention include, but are not limited to, carboxylic acids such as acetylsalicylic, acetic, ascorbic, citric, fumaric, glucuronic, glutaric, glyceric, glycocolic, glyoxylic, isocitric, isovaleric, lactic, maleic, oxaloacetic, oxalosuccinic, propionic, pyruvic, succinic, tartaric, and valeric; aluminum chloride; zinc chloride; acid salts of amino acids (or derivatives thereof) including acid salts of acetylglutamic acid, alanine, arginine, asparagine, aspartic acid, betaine, carnitine, carnosine, citrulline, creatine, glutamic acid, glycine, histidine, hydroxylysine, hydroxyproline, hypotaurine, isoleucine, leucine, lysine, methylhistidine, norleucine, ornithine, phenylalanine, proline, sarcosine, serine, taurine, threonine, tryptophan, tyrosine, and valine; certain phosphate esters including fructose 1,6 diphosphate and glucose 1,6 diphosphate may also be appropriate pH-lowering agents in certain embodiments. In particular embodiments, citric acid or tartaric acid is used as pH-lowering agent.

The quantity required of any particular pH-lowering agent or combination of pH-lowering agents may vary. Typically, a suitable amount may be determined using various tests known in the art and described herein (for example, using pH-lowering test in a solution of 10 milliliters of 0.1M sodium bicarbonate described above). As non-limiting examples, suitable amount of a pH lowering agent used in a formulation according to the present invention may be an amount of or greater than about 100 mg, 200 mg, 250 mg, 300 mg, 350 mg, 400 mg, 425 mg, 450 mg, 475 mg, 500 mg, 525 mg, 550 mg, 575 mg, 600 mg, 625 mg, 650 mg, 675, mg, 700 mg, 725 mg, 750 mg, 775 mg, 800 mg, 825 mg, 850 mg, 875 mg, 900 mg, 925 mg, 950 mg, 975 mg, or 1,000 mg. In other embodiments, the amount of citric acid used may exceed 1,000 mg.

In some embodiments, a suitable amount of a pH lowering agent (e.g., citric acid or tartaric acid) used may be measured as a percent of the total weight of a particular dosage form. As non-limiting examples, a suitable amount of a pH lowering agent used may be an amount of or greater than about 10% (e.g., of or greater than 15%, 20%, 25%, 30%, 35%, 40%, 45%, 50%, 55%, 60%, 65%, 70%, 75%, 80%, 85%, 90%, or 95%) of the total weight of a solid dosage form.

In various embodiments, a composition of the invention includes one or more absorption enhancers. As used herein, an absorption enhancer refers to an agent that increase the solubility of other components in either the aqueous or lipophilic environment into which they are released and/or enhance the uptake of an active peptide (e.g., an angiotensin (1-7) peptide) across the intestinal wall. In some embodiments, an absorption enhancer is referred to as a solubility enhancer and/or an uptake enhancer.

In some embodiments, it is possible to have a mixture of absorption enhancers wherein some provide enhanced solubility, some provide enhanced uptake, and some provide both. It is possible to have various numbers of absorption enhancers in a given embodiment including, without limitation, one, two, three, four, five, six, seven, eight, nine, or ten absorption enhancers.

Surface active agents are an example of useful absorption enhancers with properties of both solubility enhancers and uptake enhancers. In some embodiment, when surface active agents are used as absorption enhancers, they may be free flowing powders for facilitating the mixing and loading of capsules during the manufacturing process. In other embodiments when a surface active agent is used to increase the bioavailability of an angiotensin (1-7) peptide, the surface active agent may be selected from the group consisting of (a) anionic surface active agents such as cholesterol derivatives (e.g. bile acids), (b) cationic surface agents (e.g. acyl carnitines, phospholipids and the like), (c) non-ionic surface active agents, and (d) mixtures of anionic surface active agents and negative charge neutralizers, and combinations thereof. Negative charge neutralizers include but are not limited to acyl carnitines, cetyl pyridinum chloride, and the like.

In some embodiments, an acid soluble bile acid and a cationic surface active agent with be used together as absorption enhancers. Acyl carnitines (such as lauroyl carnitine), phospholipids and bile acids may be particularly effective absorption enhancers in some embodiments.

While a variety of absorption enhancers are suitable for use in various embodiments, the following exemplary list is intended to illustrate some embodiments of the present invention. Without limitation, some suitable absorption enhancers include: (a) salicylates such as sodium salicylate, 3-methoxysalicylate, 5-methoxysalicylate and homovanilate; (b) bile acids such as taurocholic, tauorodeoxycholic, deoxycholic, cholic, glycholic, lithocholate, chenodeoxycholic, ursodeoxycholic, ursocholic, dehydrocholic, fusidic, etc.; (c) non-ionic surfactants such as polyoxyethylene ethers (e.g. Brij 36T, Brij 52, Brij 56, Brij 76, Brij 96, Texaphor A6, Texaphor A14, Texaphor A60 etc.), p-t-octyl phenol polyoxyethylenes (Triton X-45, Triton X-100, Triton X-114, Triton X-305 etc.) nonylphenoxypoloxyethylenes (e.g. Igepal CO series), polyoxyethylene sorbitan esters (e.g. Tween-20, Tween-80 etc.); (d) anionic surfactants such as dioctyl sodium sulfosuccinate; (e) lyso-phospholipids such as lysolecithin and lysophosphatidylethanolamine; (f) acylcarnitines, acylcholines and acyl amino acids such as lauroylcarnitine, myristoylcarnitine, palmitoylcarnitine, lauroylcholine, myristoylcholine, palmitoylcholine, hexadecyllysine, N-acylphenylalanine, N-acylglycine etc.; g) water soluble phospholipids such as diheptanoylphosphatidylcholine, dioctylphosphatidylcholine etc.; (h) medium-chain glycerides which are mixtures of mono-, di- and triglycerides containing medium-chain-length fatty acids (caprylic, capric and lauric acids); (i) ethylene-diamine-tetraacetic acid; (j) cationic surfactants such as cetylpyridinium chloride; (k) fatty acid derivatives of polyethylene glycol such as Labrasol, Labrafac, etc.; and (l) alkylsaccharides such as lauroyl maltoside, lauroyl sucrose, myristoyl sucrose, palmitoyl sucrose, etc.

In some embodiments, the absorption enhancer(s) will be present in a quantity measured as a percent by weight, relative to the overall weight of the pharmaceutical composition (typically exclusive of enteric coating). By way of additional non-limiting example, the quantity of absorption enhancer present in an embodiment may range from 0.1 to 20 percent by weight; from 0.5 to 20 percent by weight; from 1.0 to 20 percent by weight, from 2.0 to 20 percent by weight, from 3.0 to 20 percent by weight, from 4.0 to 20 percent by weight, from from 5.0 to 20 percent by weight, from 5.0 to 15 percent by weight, from 5.0 to 14 percent by weight, from 5.0 to 13 percent by weight, from 5.0 to 12 percent by weight, from 5.0 to 12 percent by weight, from 5.0 to 11 percent by weight, from 5.0 to 10 percent by weight, from 6.0 to 10 percent by weight, from 7.0 to 10 percent by weight, from 8.0 to 10 percent by weight, from 9.0 to 10 percent by weight, from 5.0 to 9.0 percent by weight, from 5.0 to 8.0 percent by weight, from 5.0 to 7.0 percent by weight, and from 5.0 to 6.0 percent by weight.

In some embodiments, the weight ratio of pH-lowering agent(s) to absorption enhancer(s) may be about 3:1, 4:1, 5:1, 6:1, 7:1, 8:1, 9:1, 10:1, 11:1, 12:1, 13:1, 14:1, 15:1, 16:1, 17:1, 18:1, 19:1, 20:1 or between any two of the foregoing exemplary ratios. The total weight of all pH-lowering agents and the total weight of all absorption enhancers in a given pharmaceutical composition is included in the foregoing exemplary ratios. For example, if a pharmaceutical composition includes two pH-lowering agents and three absorption enhancers, the foregoing ratios will be computed on the total combined weight of both pH-lowering agents and the total combined weight of all three absorption enhancers.

In some embodiments, the absorption enhancer(s) will be soluble at acid pH, such as less than pH 5.5, and in particular, between pH 3.0 and pH 5.0.

In some embodiments, provided compositions comprise one or more protective vehicles. As used herein, a protective vehicle refers to any protective component and/or structure, such as a carrier, a layer, a coating or other vehicle, that protects an active peptide (e.g., an angiotensin (1-7) peptide) from stomach proteases. Typically, a protective vehicle dissolves eventually so that the active and other ingredients in a particular dosage form may be released. A common form of protective vehicle is an enteric coating. In some embodiments, a suitable enteric costing may prevent breakdown of the pharmaceutical composition of the invention in 0.1N HCl for at least two hours, then capable of permitting complete release of all contents of the pharmaceutical composition within thirty minutes after pH is increased to 6.3 in a dissolution bath in which said composition is rotating at 100 revolutions per minute.

Many enteric coatings are known in the art and are useful in one or more embodiments. Non-limiting examples of enteric coatings include cellulose acetate phthalate, hydroxypropyl methylethylcellulose succinate, hydroxypropyl methylcellulose phthalate, carboxyl methylethylcellulose and methacrylic acid-methyl methacrylate copolymer. In some embodiments, an angiotensin (1-7) peptide, absorption enhancers such as solubility and/or uptake enhancer(s), and pH-lowering agent(s), are included in a sufficiently viscous protective syrup to permit protected passage of the components of the embodiment through the stomach.

Suitable enteric coatings may be applied, for example, to capsules after the active and other components of the invention have been loaded within the capsule. In other embodiments, enteric coating is coated on the outside of a tablet or coated on the outer surface of particles of active components which are then pressed into tablet form, or loaded into a capsule.

In some embodiments it may be desirable that all components of the invention be released from the carrier or vehicle, and solubilized in the intestinal environment as simultaneously as possible. It may also be preferred in some embodiments that the vehicle or carrier release the active components in the small intestine where uptake enhancers that increase transcellular or paracellular transport are less likely to cause undesirable side effects than if the same uptake enhancers were later released in the colon. It will be appreciated, however, that the present invention is believed effective in the colon as well as in the small intestine. Numerous vehicles or carriers, in addition to the ones discussed above, are known in the art.

In some embodiments, it may be desirable (especially in optimizing how simultaneously the components of the invention are released) to keep the amount of enteric coating low. In some embodiments, an enteric coating adds no more than 30% to the weight of the remainder of pharmaceutical composition such as a solid dosage form (the "remainder" being the pharmaceutical composition exclusive of enteric coating itself). In other embodiments, an enteric coating adds less than 20%, less than 19%, less than 18%, less than 17%, less than 16%, less than 15%, less than 14%, less than 13%, less than 12%, less than 11%, or less than 10%. In some embodiments, a protective vehicle such as an enteric coating constitutes an amount of or less than approximately 25%, 24%, 23%, 22%, 21%, 20%, 19%, 18%, 17%, 16%, 15%, 14%, 13%, 12%, 11%, 10%, 9%, 8%, 7%, 6%, 5% of the total weight of a pharmaceutical composition (e.g., a solid dosage form).

In some embodiments, a composition is administered in a therapeutically effective amount and/or according to a dosing regimen that is correlated with a particular desired outcome (e.g., with treating or reducing risk for Marfan Syndrome or a Marfan-related disorder).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100% or more. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100%. Alternatively or additionally, in some embodiments, an appropriate dose or amount is determined through use of one or more in vitro or in vivo assays to help identify desirable or optimal dosage ranges or amounts to be administered.

In various embodiments, an Ang (1-7) peptide or angiotensin (1-7) receptor agonist is administered at a therapeutically effective amount. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

Therapeutically effective dosage amounts of angiotensin (1-7) peptides or angiotensin (1-7) receptor agonists, including derivatives, analogs, and/or salts may be present in varying amounts in various embodiments. For example, in some embodiments, a therapeutically effective amount of an angiotensin (1-7) peptide may be an amount ranging from about 10-1000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, an angiotensin (1-7) peptide or angiotensin (1-7) receptor agonist is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, an angiotensin (1-7) peptide or angiotensin (1-7) receptor agonist is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg. In some embodiments, the therapeutically effective amount described herein is provided in one dose. In some embodiments, the therapeutically effective amount described herein is provided in one day.

In other embodiments, a therapeutically effective dosage amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight. In some embodiments, the therapeutically effective amount described herein is provided in one dose. In some embodiments, the therapeutically effective amount described herein is provided in one day.

In still other embodiments, a therapeutically effective dosage amount may be, for example, about 0.001 mg/kg weight to about 1 mg/kg weight, e.g. from about 0.001 mg/kg weight to about 0.9 mg/kg weight, from about 0.001 mg/kg weight to about 0.8 mg/kg weight, from about 0.001 mg/kg weight to about 0.8 mg/kg weight, from about 0.001 mg/kg weight to about 0.7 mg/kg weight, from about 0.001 mg/kg weight to about 0.6 mg/kg weight, from about 0.001 mg/kg weight to about 0.5 mg/kg weight, from about 0.01 mg/kg weight to about 1 mg/kg weight, from about 0.01 mg/kg weight to about 0.9 mg/kg weight, from about 0.01 mg/kg weight to about 0.8 mg/kg weight, from about 0.01 mg/kg weight to about 0.7 mg/kg weight, from about 0.01 mg/kg weight to about 0.6 mg/kg weight, from about 0.01 mg/kg weight to about 0.5 mg/kg weight, from about 0.02 mg/kg weight to about 1 mg/kg weight, from about 0.02 mg/kg weight to about 0.9 mg/kg weight, from about 0.02 mg/kg weight to about 0.8 mg/kg weight, from about 0.02 mg/kg weight to about 0.7 mg/kg weight, from about 0.02 mg/kg weight to about 0.6 mg/kg weight, from about 0.02 mg/kg weight to about 0.5 mg/kg weight, from about 0.03 mg/kg weight to about 1 mg/kg weight, from about 0.03 mg/kg weight to about 0.9 mg/kg weight, from about 0.03 mg/kg weight to about 0.8 mg/kg weight, from about 0.03 mg/kg weight to about 0.7 mg/kg weight, from about 0.03 mg/kg weight to about 0.6 mg/kg weight, from about 0.03 mg/kg weight to about 0.5 mg/kg weight, from about 0.04 mg/kg weight to about 1 mg/kg weight, from about 0.04 mg/kg weight to about 0.9 mg/kg weight, from about 0.04 mg/kg weight to about 0.8 mg/kg weight, from about 0.04 mg/kg weight to about 0.7 mg/kg weight, from about 0.04 mg/kg weight to about 0.6 mg/kg weight, from about 0.04 mg/kg weight to about 0.5 mg/kg weight, from about 0.05 mg/kg weight to about 1 mg/kg weight, from about 0.05 mg/kg weight to about 0.9 mg/kg weight, from about 0.05 mg/kg weight to about 0.8 mg/kg weight, from about 0.05 mg/kg weight to about 0.7 mg/kg weight, from about 0.05 mg/kg weight to about 0.6 mg/kg weight, from about 0.05 mg/kg weight to about 0.5 mg/kg weight. In some embodiments, the therapeutically effective amount described herein is provided in one dose. In some embodiments, the therapeutically effective amount described herein is provided in one day.

In still other embodiments, a therapeutically effective dosage amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual.

In some embodiments, the angiotensin (1-7) peptide is administered at an effective dose ranging from about 1-1,000 µg/kg/day (e.g., ranging from about 1-900 µg/kg/day, 1-800 µg/kg/day, 1-700 µg/kg/day, 1-600 µg/kg/day, 1-500 µg/kg/day, 1-400 µg/kg/day, 1-300 µg/kg/day, 1-200 µg/kg/day, 1-100 µg/kg/day, 1-90 µg/kg/day, 1-80 µg/kg/day, 1-70 µg/kg/day, 1-60 µg/kg/day, 1-50 µg/kg/day, 1-40 µg/kg/day, 1-30 µg/kg/day, 1-20 µg/kg/day, 1-10 µg/kg/day). In some embodiments, the angiotensin (1-7) peptide is administered at an effective dose ranging from about 1-500 µg/kg/day. In some embodiments, the angiotensin (1-7) peptide is administered at an effective dose ranging from about 1-100 µg/kg/day. In some embodiments, the angiotensin (1-7) peptide is administered at an effective dose ranging from about 1-60 µg/kg/day. In some embodiments, the angiotensin (1-7) peptide is administered at an effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 ug/kg/day.

Routes of Administration

An angiotensin (1-7) peptide or angiotensin (1-7) receptor agonist as described herein (or a composition or medicament containing an angiotensin (1-7) peptide or Angiotensin (1-7) receptor agonist as described herein) may be administered by any appropriate route. In some embodiments, the angiotensin (1-7) peptide is administered parenterally. In some embodiments, the parenteral administration is selected from intravenous, intradermal, inhalation, transdermal (topical), intraocular, intramuscular, subcutaneous, intramuscular, and/or transmucosal administration. In some embodiments, an angiotensin (1-7) peptide or angiotensin (1-7) receptor agonist as described herein is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, an angiotensin (1-7) peptide or angiotensin (1-7) receptor agonist as described herein is administered intravenously. In other embodiments, an angiotensin (1-7) peptide or angiotensin (1-7) receptor agonist as described herein is administered by direct administration to a target tissue, such as heart or muscle (e.g., intramuscular), tumor (intratumorally), nervous system (e.g., direct injection into the brain; intraventricularly; intrathecally). Alternatively, an angiotensin (1-7) peptide or angiotensin (1-7) receptor agonist as described herein (or a composition or medicament containing an angiotensin (1-7) peptide or angiotensin (1-7) receptor agonist as described herein) can be administered by inhalation, parenterally, intradermally, transdermally, or transmucosally (e.g., orally or nasally). More than one route can be used concurrently, if desired.

In some embodiments, an angiotensin (1-7) peptide or angiotensin (1-7) receptor agonist as described herein is administered orally. In some embodiments, the present invention provides solid dosage forms of an angiotensin (1-7) peptide or angiotensin (1-7) receptor agonist as described herein for oral administration including (a) an angiotensin (1-7) peptide, (b) at least one pharmaceutically acceptable pH-lowering agent, (c) at least one absorption enhancer effective to promote bioavailability of the angiotensin (1-7) peptide, and (d) a protective vehicle. In some embodiments, the solid dosage form is a capsule or tablet. Various methods and ingredients for making oral formulations are known in the art and it is expected that one of skill would be able to determine which of these methods and ingredients will be compatible with the invention as described in this specification and/or in U.S. Provisional Patent Application Ser. No. 61/701,972, filed on Sep. 17, 2012, the disclosure of which is hereby incorporated in its entirety. Such methods and ingredients are also contemplated as within the scope of the present invention.

Dosing Schedules

Various embodiments may include differing dosing regimen. In some embodiments, the angiotensin (1-7) peptide or angiotensin (1-7) receptor agonist is administered via continuous infusion. In some embodiments, the continuous infusion is intravenous. In other embodiments, the continuous infusion is subcutaneous. Alternatively or additionally, in some embodiments, the angiotensin (1-7) peptide or angiotensin (1-7) receptor agonist is administered bimonthly, monthly, twice monthly, triweekly, biweekly, weekly, twice weekly, thrice weekly, daily, twice daily, or on another clinically desirable dosing schedule. The dosing regimen for a single subject need not be at a fixed interval, but can be varied over time, depending on the needs of the subject.

Combination Therapies

In some embodiments, an Ang (1-7) peptide or angiotensin (1-7) receptor agonist will be used as a part of a combination therapy. It is contemplated that any known therapeutic or treatment for one or more brain conditions may be used with one or more Ang (1-7) peptides or angiotensin (1-7) receptor agonists as disclosed herein. Exemplary compounds that may be used with one or more Ang (1-7) peptides or angiotensin (1-7) receptor agonists as a combination therapy include, but are not limited to, beta blockers, calcium channel blockers, ACE inhibitors, angiotensin II receptor antagonists (e.g. losartan), anticoagulants, and combinations thereof.

Kits

In some embodiments, the present invention further provides kits or other articles of manufacture which contains an Ang (1-7) peptide, an angiotensin (1-7) receptor agonist or a formulation containing the same and provides instructions for its reconstitution (if lyophilized) and/or use. Kits or other articles of manufacture may include a container, a syringe, vial and any other articles, devices or equipment useful in administration (e.g., subcutaneous, by inhalation). Suitable containers include, for example, bottles, vials, syringes (e.g., pre-filled syringes), ampules, cartridges, reservoirs, or lyojects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may holds formulations and a label on, or associated with, the container that may indicate directions for reconstitution and/or use. For example, the label may indicate that the formulation is reconstituted to concentrations as described above. The label may further indicate that the formulation is useful or intended for, for example, subcutaneous administration. In some embodiments, a container may contain a single dose of a stable formulation containing an Ang (1-7) peptide or angiotensin (1-7) receptor agonist. In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 20 mg/ml, at least 30 mg/ml, at least 40 mg/ml, at least 50 mg/ml, at least 75 mg/ml, at least 100 mg/ml). Kits or other articles of manufacture may further include other materials desirable from a commercial and user standpoint, including other buffers, diluents, filters, needles, syringes, and package inserts with instructions for use. In some embodiments, kits or other articles of manufacture may include an instruction for self-administration.

EXAMPLES

Example 1

Angiotensin (1-7) Peptides in Decreasing Aortic Ring Dilation

In this Example, FBN1$^{C1039G/+}$ mice, a known and accepted model of Marfan Syndrome, are used to assess the effects of several angiotensin (1-7) peptides and an angiotensin (1-7) receptor agonist, AVE0991, on the aortic dilation typically seen in these mice. See, Xiong et al., Doxycycline delays aneurysm rupture in a mouse model of Marfan Syndrome, 2008, *J. Vascular Surg* 47:166-172. This mutation of the fibrillin-1 (FBN1) gene leads these mice to develop progressive aortic root dilation with sporadic aortic dissections throughout life, often leading to death.

In this example, three angiotensin (1-7) peptides, namely, TXA127 (SEQ ID NO:1), PanCyte (SEQ ID NO:22), and TXA301 (SEQ ID NO: 2) and a small molecule angiotensin (1-7) receptor agonist AVE0991 are used to examine their effect on the progression of aortic dilation over time. Specifically, 110 FBN1$^{C1039G/+}$ mice, (10 per group) are placed into one of the groups outlined in Table 1 below.

TABLE 1

Study Design

| Group | Agent | Dose | N | Route of Admin. | Dosing Frequency |
|---|---|---|---|---|---|
| 1 | Vehicle Control (PBS) | PBS | 10 | Subcutaneous | Daily |
| 2 | TXA127 | 50 μg/kg/day | 10 | Subcutaneous | Daily |
| 3 | TXA127 | 500 μg/kg/day | 10 | Subcutaneous | Daily |
| 4 | TXA127 | 1,000 μg/kg/day | 10 | Subcutaneous | Daily |
| 5 | PanCyte | 50 μg/kg/day | 10 | Subcutaneous | Daily |
| 6 | PanCyte | 500 μg/kg/day | 10 | Subcutaneous | Daily |
| 7 | PanCyte | 1,000 μg/kg/day | 10 | Subcutaneous | Daily |
| 8 | TXA301 | 50 μg/kg/day | 10 | Subcutaneous | Daily |
| 9 | TXA301 | 500 μg/kg/day | 10 | Subcutaneous | Daily |
| 10 | TXA301 | 1,000 μg/kg/day | 10 | Subcutaneous | Daily |
| 11 | AVE0991 | 300 μg/kg/day | 10 | Subcutaneous | Daily |

In this example, TXA127, TXA301, PanCyte, and AVE0991 are prepared in saline and administrated subcutaneously via subscapular injection at a dose volume of 100 μl/mouse daily for twenty-eight days. Dosing solutions are prepared fresh every three days.

One week after the final injection, each animal is sacrificed, and the aortic ring is removed and analyzed to determine if administration of an angiotensin (1-7) peptide or angiotensin (1-7) receptor agonist is sufficient to decrease the degree of aortic dilation of treated mice as compared to control animals.

It is expected that administration of an angiotensin (1-7) peptide decreases aortic ring dilation in FBN1$^{C1039G/+}$ mice. Administration of an angiotensin (1-7) peptide will also decrease the degree of joint laxity in FBN1$^{C1039G/+}$ mice.

Example 2

TXA127 in Decreasing Aortic Aneurysm Growth

In this Example, the ability of TXA127 to attenuate aortic root growth typically observed in Marfan sufferers is described. Aortic root growth is one of the most serious, and often deadly, effects of the disease.

In this Example, a total of 20 mice were used, with 8 mice being wild-type and 12 being Fbn1$^{C1039G+}$ mice, also referred to as "Marfan mice", that are each homozygous for a fibrillin-1 (Fbn1) allele encoding a cysteine substitution, Cys1039Gly (C1039G), in an epidermal growth factor-like domain of Fbn1 (Fbn1$^{C1039G/+}$).

The Fbn1C1039G mice are a well-accepted model of Marfan Syndrome and the Fbn1 mutation is the most common class of mutation causing Marfan Syndrome. Typically, the aortic root in Fbn1C1039G mice undergoes progressive dilatation, evident as early as 2 weeks of age. By 7 weeks of age, the aortic root in the mutant mice is significantly larger than that in wild-type mice. This observed size difference generally becomes more pronounced over time. Histologic analysis of 14-week-old Fbn1C1039G mice reveals aberrant thickening of the aortic media with fragmentation and disarray of elastic fibers. In addition, Fbn1C1039G mice show increased collagen deposition, which is an indirect marker of increased TGF-β signaling. Phosphorylation and subsequent nuclear translocation of Smad2 (pSmad2) and Erk1/2 (pERK1/2), which are induced by TGF-β signaling, are markedly increased in the aortic media of Fbn1C1039G mice relative to wild-type mice.

In order to determine the effects of angiotensin (1-7) peptides, here TXA127, on the normal course of disease development, both wild-type and Marfan mice were each separated into two groups once the mice reached 2 months of age. In each of the wild-type mice and Marfan mice, the placebo control group received daily subcutaneous saline injections for 60 days, while the TXA127 group received daily subcutaneous injections of TXA127 at a dose of 500 µg/kg/day for 60 days.

The primary endpoint of this study was degree of aortic growth observed over the 60 day treatment period, as measured by in vivo echocardiography. A baseline echocardiogram was performed just prior to the beginning of the treatment period and then again just prior to sacrifice. After the 60 day treatment period, mice were sacrificed and tissue samples were taken for histological and other analysis.

As shown in FIG. 1, in Marfan mice, treatment with 500 µg/kg/day of TXA127 resulted in a highly significant reduction in the degree of aortic root growth as compared to Marfan mice treated with placebo. In fact, the data show that aortic root growth was essentially eliminated in the TXA127 group. FIG. 1 also shows that treatment with TXA127 has no statistically significant effect on the aortic root growth of wild type mice as compared to wild type mice treated with placebo.

This Example represents the first time that an Angiotensin (1-7) peptide has been shown to have a significant effect on one of the most deadly symptoms of Marfan Syndrome. Accordingly, several embodiments of the present invention provide a powerful and entirely new class of treatments for Marfan sufferers.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of treatment of Marfan Syndrome comprising administering to a subject suffering from Marfan Syndrome an angiotensin (1-7) peptide, wherein the treatment of Marfan Syndrome results in at least one of aortic enlargement and aortic dissection being reduced in intensity, severity, duration, or frequency or delayed in onset; and
    wherein the angiotensin (1-7) peptide comprises the sequence of SEQ ID NO: 1 or SEQ ID NO: 2.

2. The method of claim 1, wherein the angiotensin (1-7) peptide is administered parenterally.

3. The method of claim 2, wherein the parenteral administration is selected from intravenous, intradermal, inhalation, transdermal, intraocular, intramuscular, subcutaneous, intramuscular, or transmucosal administration.

4. The method of claim 1, wherein the angiotensin (1-7) peptide is administered orally.

5. The method of claim 1, wherein the angiotensin (1-7) peptide is administered monthly, weekly, daily, or at variable intervals.

6. The method of claim 1, wherein the angiotensin (1-7) peptide is administered at an effective dose ranging from about 1-1,000 μg/kg/day.

7. The method of claim 1, wherein the angiotensin (1-7) peptide is administered at an effective dose ranging from about 50-500 μg/kg/day.

8. The method of claim 1, wherein the angiotensin (1-7) peptide is administered at an effective dose ranging from about 400-500 μg/kg/day.

9. The method of claim 1, wherein the angiotensin (1-7) peptide is administered in combination with one or more Marfan Syndrome medications.

10. The method of claim 9, wherein the one or more Marfan Syndrome medications is selected from the group consisting of beta blockers, calcium channel blockers, ACE inhibitors, angiotensin II receptor antagonists, anticoagulants, and combinations thereof.

11. The method of claim 1, wherein the angiotensin (1-7) peptide comprises the naturally-occurring Angiotensin (1-7) amino acid sequence of $Asp^1$-$Arg^2$-$Val^3$-$Tyr^4$-$Ile^5$-$His^6$-$Pro^7$ (SEQ ID NO:1).

12. The method of claim 1, wherein the angiotensin (1-7) peptide comprises the amino acid sequence of $Asp^1$-$Arg^2$-$Val^3$-$Ser^4$-$Ile^5$-$His^6$-$Cys^7$ (SEQ ID NO: 2).

13. The method of claim 1, wherein the angiotensin (1-7) peptide comprises one or more chemical modifications to increase protease resistance, serum stability and/or bioavailability.

14. The method of claim 13, wherein the one or more chemical modifications comprise pegylation.

* * * * *

SEQUENCE LISTING

```
<160> NUMBER OF SEQ ID NOS: 24

<210> SEQ ID NO 1
<211> LENGTH: 7
<212> TYPE: PRT
<213> ORGANISM: Unknown
<220> FEATURE:
<223> OTHER INFORMATION: Description of Unknown: Naturally occurring
      Angiotensin (1-7) peptide

<400> SEQUENCE: 1

Asp Arg Val Tyr Ile His Pro
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Arg Val Ser Ile His Cys
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Arg Val Tyr Ile His Pro Phe His Leu Val Ile
1               5                   10

<210> SEQ ID NO 4
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid, any dicarboxylic acid, Asp,
      Glu, Asn, Acpc, Ala, Me2Gly, Pro, Bet, Glu, Gly, Asp,
      Sar, Suc or any negatively-charged amino acid
<220> FEATURE:
<221> NAME/KEY: MOD_RES
<222> LOCATION: (2)..(2)
<223> OTHER INFORMATION: Arg, Lys, Ala, Cit, Orn, acetylated Ser, Sar,
      D-Arg D-Lys or any positively-charged amino acid
<220> FEATURE:
<221> NAME/KEY: MOD_RES
<222> LOCATION: (3)..(3)
<223> OTHER INFORMATION: Val, Ala, Leu, Nle, Ile, Gly, Lys, Pro,
      HydroxyPro, Aib, Acpc, Tyr or any aliphatic amino acid
<220> FEATURE:
<221> NAME/KEY: MOD_RES
<222> LOCATION: (4)..(4)
<223> OTHER INFORMATION: Tyr, Tyr(PO3), Thr, Ser, homoSer, azaTyr, Ala
      or any hydroxyl-substituted amino acid
<220> FEATURE:
<221> NAME/KEY: MOD_RES
<222> LOCATION: (5)..(5)
<223> OTHER INFORMATION: Ile, Ala, Leu, norLeu, Val, Gly or any
      aliphatic amino acid
<220> FEATURE:
<221> NAME/KEY: MOD_RES
<222> LOCATION: (6)..(6)
<223> OTHER INFORMATION: His, Arg, 6-NH2-Phe or any fully or partially
      positively-charged amino acid
<220> FEATURE:
<221> NAME/KEY: MOD_RES
<222> LOCATION: (7)..(7)
<223> OTHER INFORMATION: Cys, Pro or Ala
<220> FEATURE:
<223> OTHER INFORMATION: see specification as filed for detailed
      description of substitutions and preferred embodiments

<400> SEQUENCE: 4

Xaa Xaa Xaa Xaa Xaa Xaa Xaa
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle

<400> SEQUENCE: 5

Asp Arg Leu Tyr Ile His Pro
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Arg Val Ser Ile His Cys
1               5
```

```
<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(7)
<223> OTHER INFORMATION: Cyclized thioether bridge between positions
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: see specification as filed for detailed
      description of substitutions and preferred embodiments

<400> SEQUENCE: 7

Asp Arg Val Xaa Ile His Xaa
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(7)
<223> OTHER INFORMATION: Cyclized thioether bridge between positions
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: see specification as filed for detailed
      description of substitutions and preferred embodiments

<400> SEQUENCE: 8

Asp Arg Leu Xaa Ile His Xaa Phe His Leu
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
```

```
<222> LOCATION: (4)..(7)
<223> OTHER INFORMATION: Cyclized thioether bridge between positions
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: see specification as filed for detailed
      description of substitutions and preferred embodiments

<400> SEQUENCE: 9

Asp Arg Leu Xaa Ile His Xaa Phe
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: Any amino acid
<220> FEATURE:
<221> NAME/KEY: misc_feature
<222> LOCATION: (3)..(6)
<223> OTHER INFORMATION: Cyclized thioether bridge between positions
<220> FEATURE:
<221> NAME/KEY: MOD_RES
<222> LOCATION: (6)..(6)
<223> OTHER INFORMATION: Any amino acid
<220> FEATURE:
<223> OTHER INFORMATION: see specification as filed for detailed
      description of substitutions and preferred embodiments

<400> SEQUENCE: 10

Arg Leu Xaa Ile His Xaa Phe
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: Any amino acid
<220> FEATURE:
<221> NAME/KEY: misc_feature
<222> LOCATION: (2)..(5)
<223> OTHER INFORMATION: Cyclized thioether bridge between positions
<220> FEATURE:
<221> NAME/KEY: MOD_RES
<222> LOCATION: (5)..(5)
<223> OTHER INFORMATION: Any amino acid
<220> FEATURE:
<223> OTHER INFORMATION: see specification as filed for detailed
      description of substitutions and preferred embodiments

<400> SEQUENCE: 11

Leu Xaa Ile His Xaa Phe
```

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(7)
<223> OTHER INFORMATION: Cyclized thioether bridge between positions
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: see specification as filed for detailed
      description of substitutions and preferred embodiments

<400> SEQUENCE: 12

Asp Arg Leu Xaa Ile His Xaa
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(7)
<223> OTHER INFORMATION: Cyclized thioether bridge between positions
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: see specification as filed for detailed
      description of substitutions and preferred embodiments

<400> SEQUENCE: 13

Asp Arg Leu Xaa Ile His Xaa Phe His
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

```
<223> OTHER INFORMATION: Any amino acid
<220> FEATURE:
<221> NAME/KEY: MOD_RES
<222> LOCATION: (2)..(2)
<223> OTHER INFORMATION: Any positively-charged amino acid
<220> FEATURE:
<221> NAME/KEY: MOD_RES
<222> LOCATION: (3)..(3)
<223> OTHER INFORMATION: Any aliphatic amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(7)
<223> OTHER INFORMATION: Cyclized thioether bridge between positions
<220> FEATURE:
<221> NAME/KEY: MOD_RES
<222> LOCATION: (5)..(5)
<223> OTHER INFORMATION: Any aliphatic amino acid
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: see specification as filed for detailed
      description of substitutions and preferred embodiments

<400> SEQUENCE: 14

Xaa Xaa Xaa Xaa Xaa His Xaa
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Abu

<400> SEQUENCE: 15

Asp Arg Val Xaa Ile His Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Arg Val Ala Ile His Ala
1               5

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid or absent
<220> FEATURE:
```

```
<221> NAME/KEY: MOD_RES
<222> LOCATION: (2)..(2)
<223> OTHER INFORMATION: Any positively charged amino acid or absent
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(7)
<223> OTHER INFORMATION: Cyclized thioether bridge between positions
<220> FEATURE:
<221> NAME/KEY: MOD_RES
<222> LOCATION: (5)..(5)
<223> OTHER INFORMATION: Any aliphatic amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid except Pro or absent
<220> FEATURE:
<221> NAME/KEY: MOD_RES
<222> LOCATION: (9)..(9)
<223> OTHER INFORMATION: May or may not be present
<220> FEATURE:
<221> NAME/KEY: MOD_RES
<222> LOCATION: (10)..(10)
<223> OTHER INFORMATION: Any aliphatic amino acid or absent
<220> FEATURE:
<223> OTHER INFORMATION: see specification as filed for detailed
      description of substitutions and preferred embodiments

<400> SEQUENCE: 17

Xaa Xaa Leu Xaa Xaa His Xaa Xaa His Xaa
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Abu

<400> SEQUENCE: 18

Asp Arg Leu Xaa Ile His Ala
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
```

```
<400> SEQUENCE: 19

Asp Arg Leu Ala Ile His Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Abu

<400> SEQUENCE: 20

Asp Arg Leu Xaa Ile His Ala Ile
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle

<400> SEQUENCE: 21

Asp Arg Leu Ala Ile His Ala Ile
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(7)
<223> OTHER INFORMATION: Cyclized thioether bridge between positions

<400> SEQUENCE: 22

Asp Arg Val Ser Ile His Cys
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Arg Val Tyr Ile His Pro Phe His
1               5

<210> SEQ ID NO 24
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Arg Val Tyr Ile His Pro
1               5
```